United States Patent
Halperin

(10) Patent No.: US 7,439,330 B2
(45) Date of Patent: Oct. 21, 2008

(54) ANTI-GLYCATED CD59 ANTIBODIES AND USES THEREOF

(75) Inventor: Jose Halperin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 114 days.

(21) Appl. No.: 10/870,342

(22) Filed: Jun. 17, 2004

(65) Prior Publication Data

US 2005/0032128 A1    Feb. 10, 2005

(51) Int. Cl.
C07K 16/40    (2006.01)
G01N 33/53    (2006.01)

(52) U.S. Cl. .............. 530/388.2; 530/389.1; 530/391.3; 435/7.9

(58) Field of Classification Search .............. 530/388.2, 530/389.1, 391.3; 435/7.9
See application file for complete search history.

(56) References Cited

U.S. PATENT DOCUMENTS

| | | | |
|---|---|---|---|
| 4,281,061 A | | 7/1981 | Zuk et al. |
| 4,816,567 A | | 3/1989 | Cabilly et al. |
| 5,225,539 A | | 7/1993 | Winter |
| 5,470,759 A | * | 11/1995 | Sugiyama et al. ............ 436/541 |
| 5,585,089 A | | 12/1996 | Queen et al. |
| 5,693,762 A | | 12/1997 | Queen et al. |
| 5,789,208 A | * | 8/1998 | Sharon ..................... 435/91.41 |
| 5,853,703 A | * | 12/1998 | Cerami et al. ................. 424/53 |
| 5,859,205 A | | 1/1999 | Adair et al. |
| 6,835,545 B2 | | 12/2004 | Halperin |
| 7,049,082 B2 | | 5/2006 | Halperin |
| 2004/0219606 A1 | | 11/2004 | Halperin |
| 2006/0257936 A1 | | 11/2006 | Halperin |

FOREIGN PATENT DOCUMENTS

| | | |
|---|---|---|
| EP | 0394035 | 10/1990 |
| EP | 1789449 | 5/2007 |
| WO | WO 98/19711 | 5/1998 |
| WO | WO 04/106941 | 12/2004 |
| WO | WO 2006/009533 A | 1/2006 |
| WO | WO 2006/086098 A2 | 8/2006 |

OTHER PUBLICATIONS

Suzuki, D et al. Journal of Diabetes and Its Complications [1996] 10(6):314-319.*
Takata, I. et al. Biochem. Biophys. Res. Comm. [1996] 219:243-248.*
Harlow et al. Antibodies: A Laboratory Manual. [1988] pp. 321-323.*
Acosta, et al., Proc Natl Acad Sci 97, 5450-5455 (2000).
Acosta, et al., Complement and complement regulatory proteins as potential molecular targets for vascular diseases. Current Pharmaceutical Design, 10, 1-9, 2004.
Benzaquen, et al., J. Exp. Med. 179, 985-992 (1994).
Bodian, et al., Mutational analysis of the active site and antibody epitopes of the complement-inhibitory glycoprotein, CD59. J. Exp. Med, 185(3): 507-516, 1997.
Davies, et al., J. Exp. Med,. 170(3), 637-654 (1989).
Fletcher, et al., Structure, 2, 185-199 (1994).
Halperin, et al., J. Clin. Invest., 91, 1974-1978 (1993).
Halperin, et al., J. Clin. Invest., 80, 128-137 (1987).
Halperin, et al, Blood 81, 200-205 (1993).
Hughes, et al., Biochem. J., 284, 169-176 (1992).
Lapolla, et al., The role of mass spectrometry in the study of non-enzymatic protein glycation in diabetes. Mass Spectrometry Reviews, 19: 279-304, 2000.
Myint, et al., Biochim. Biophys. Acta 1272, 73-79 (1995).
Philbrick, et al., Eur. J. Immunol., 20, 87-92 (1990).
Rosoklija, et al., Acta Neuro, 99, 55-62 (2000).
Van Den Berg, et al., Immunology 78, 349-357 (1993).
Zhao, et al., J. Biol. Chem. 266, 13418-13422 (1991).
Zhang, J. et al., Early Complement Activation and Decreased Levels Of Glycosylphosphatidylinositol-Anchored Complement Inhibitors in Human and Experimental Diabetic Retinopathy. Diabetes, 51: 3499-3504, 2002.
Qin, X. et al., A Role of Glycated Human Cd59 and the Complement System in the Pathogenesis of Chronic Vascular Complications of Diabetes. International Immunopharmacology, 2: 1382-1383, 2002.
Qin X. et al., Genomic Structure, Functional Comparison, and Tissue Distribution Of Mouse Cd59a and Cd59b. Mammalian Genome, 12: 582-589, 2001.
PCT/US2006/000310, International Search Report, Oct. 30, 2006.
PCT/US2006/000310, International Preliminary Report on Patentability, Jul. 10, 2007.
PCT/US2004/019392, International Search Report, Jun. 6, 2005.
PCT/US2004/019392, International Preliminary Report on Patentability, Dec. 20, 2006.

* cited by examiner

Primary Examiner—David A Saunders
Assistant Examiner—F. Pierre VanderVegt
(74) Attorney, Agent, or Firm—Wolf, Greenfield & Sacks, P.C.

(57) ABSTRACT

The invention includes antibodies or antigen-binding fragments thereof which bind specifically to glycated CD59, compositions containing one or a combination of such antibodies or antigen-binding fragments thereof, hybridoma cell lines that produce the antibodies, and methods of producing and using the antibodies or antigen-binding fragments thereof for diagnosis and treatment of diabetic conditions and diabetic-associated conditions.

15 Claims, 7 Drawing Sheets

Specificity of the anti-glycated CD59 antibody

Fig. 3A Western blot

Fig. 3B ELISA

| | OD |
|---|---|
| CD59 | 0.083 |
| CD59$_{glu}$ | 0.212 |
| Alb$_{glu}$ | 0.078 |

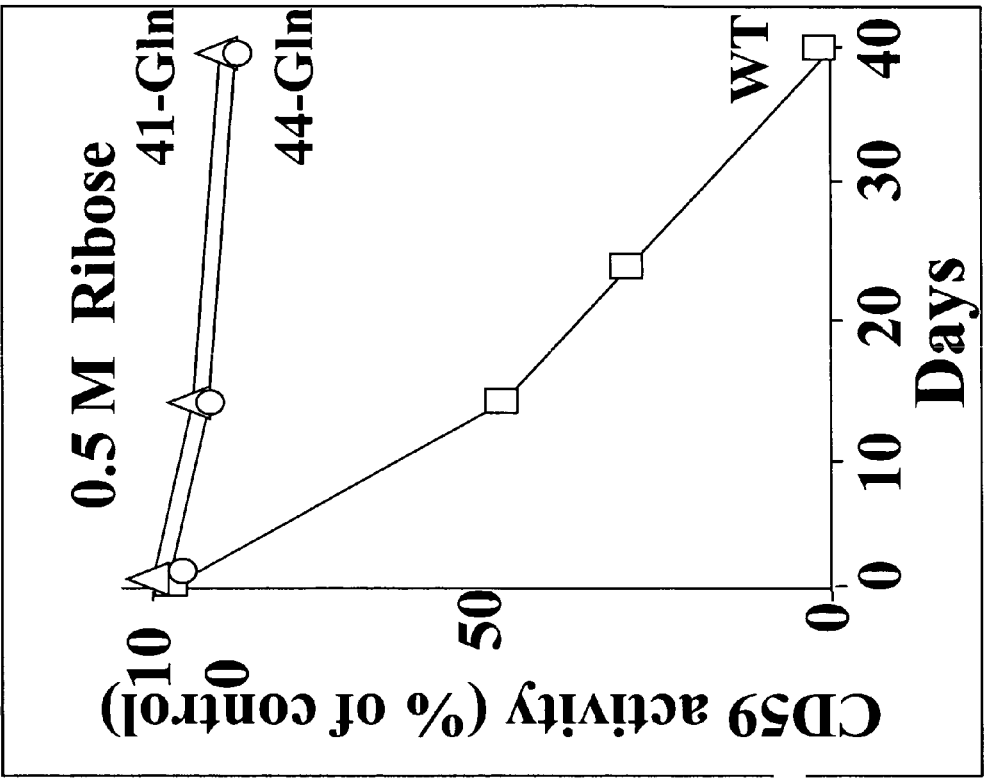
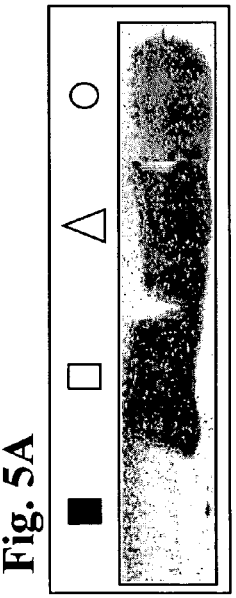
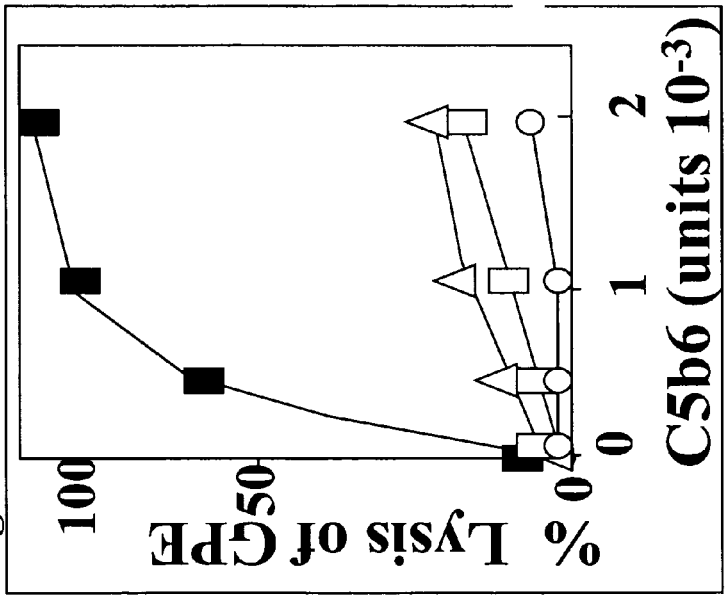
Fig. 5A
Fig. 5B
Fig. 5C

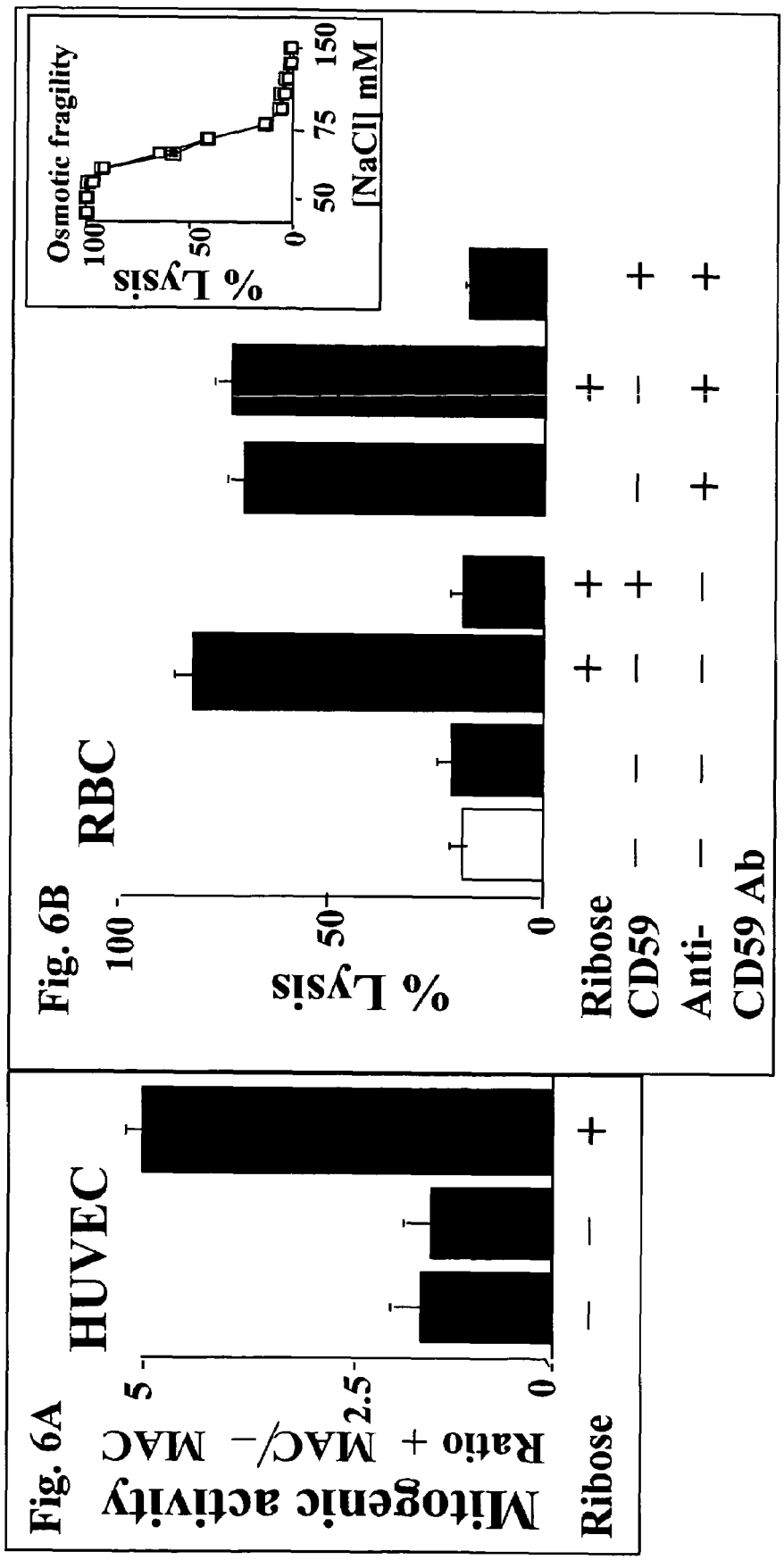

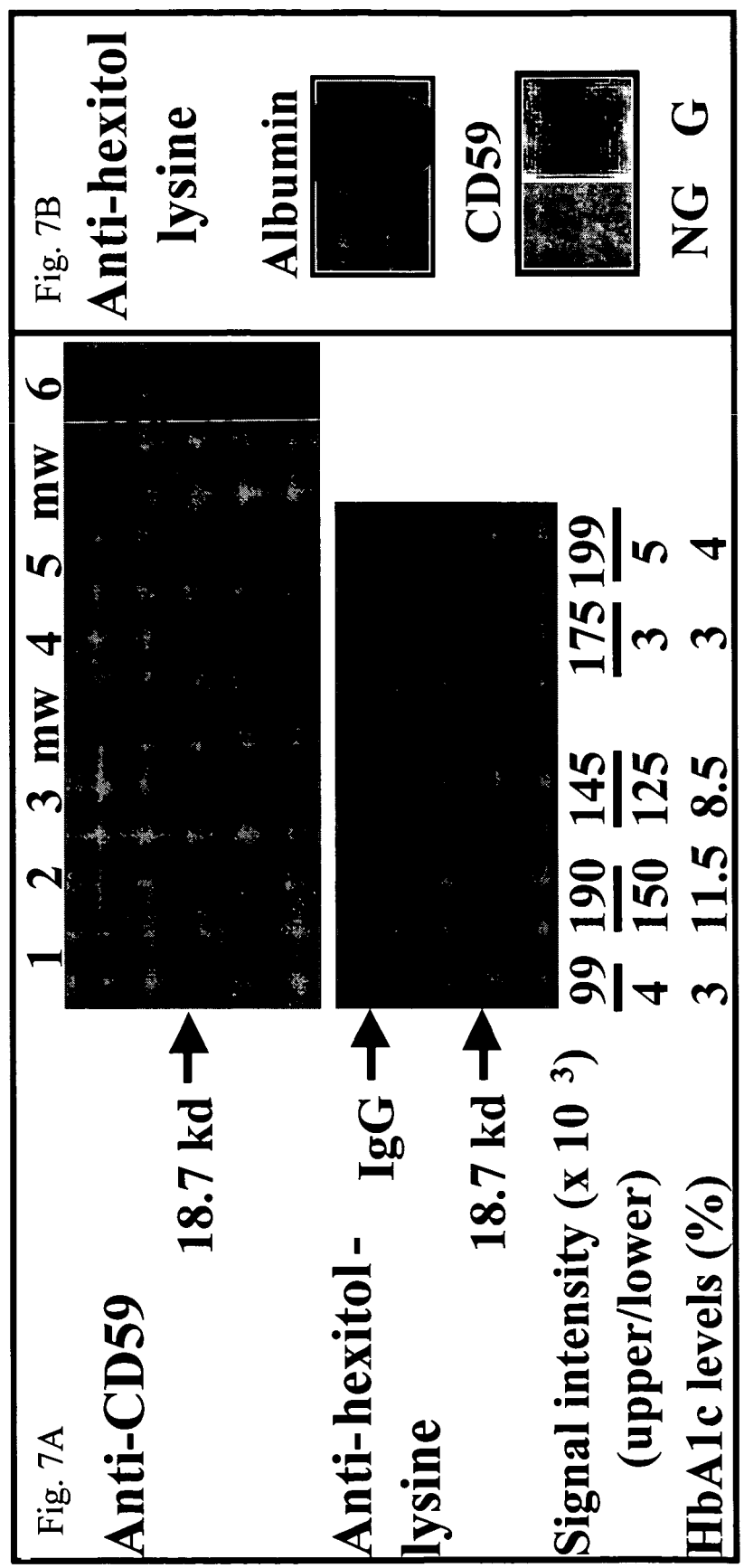

SEQUENCE LISTING

<160> NUMBER OF SEQ ID NOS: 49

<210> SEQ ID NO 1
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Lys is glycated

<400> SEQUENCE: 1

Trp Lys Phe Glu His
1               5

<210> SEQ ID NO 2
<211> LENGTH: 5
<212> TYPE: PRT
<213> ORGANISM: Homo sapiens

<400> SEQUENCE: 2

Trp Lys Phe Glu His
1               5

<210> SEQ ID NO 3
<211> LENGTH: 14
<212> TYPE: PRT
<213> ORGANISM: Homo sapiens
<220> FEATURE:
<221> NAME/KEY: misc_feature
<222> LOCATION: (5)..(5)
<223> OTHER INFORMATION: Lys is glycated

<400> SEQUENCE: 3

Asn Lys Ala Trp Lys Phe Glu His Ala Asn Phe Asn Asp Cys
1               5                   10

<210> SEQ ID NO 4
<211> LENGTH: 13
<212> TYPE: PRT
<213> ORGANISM: Homo sapiens

<400> SEQUENCE: 4

Asn Lys Cys Trp Lys Phe Glu His Cys Asn Phe Asn Asp
1               5                   10

<210> SEQ ID NO 5
<211> LENGTH: 128
<212> TYPE: PRT
<213> ORGANISM: Homo sapiens

<400> SEQUENCE: 5

Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
        35                  40                  45

Asp Ala Cys Leu Ile Thr Lys Ala Gly Leu Gln Val Tyr Asn Lys Cys
    50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn Gly Gly Thr Ser Leu Ser Glu Lys Thr Val
            100                 105                 110

Leu Leu Leu Val Thr Pro Phe Leu Ala Ala Ala Trp Ser Leu His Pro
        115                 120                 125

<210> SEQ ID NO 6
<211> LENGTH: 103
<212> TYPE: PRT
<213> ORGANISM: Homo sapiens

<400> SEQUENCE: 6

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Leu Val Thr Pro Phe Leu Ala
                85                  90                  95

Ala Ala Trp Ser Leu His Pro
            100

<210> SEQ ID NO 7
<211> LENGTH: 103
<212> TYPE: PRT
<213> ORGANISM: Homo sapiens
<220> FEATURE:
<221> NAME/KEY: misc_feature
<222> LOCATION: (41)..(41)
<223> OTHER INFORMATION: Lys is glycated

<400> SEQUENCE: 7

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Leu Val Thr Pro Phe Leu Ala
                85                  90                  95

Ala Ala Trp Ser Leu His Pro
            100

<210> SEQ ID NO 8
<211> LENGTH: 103
<212> TYPE: PRT
<213> ORGANISM: Homo sapiens
<220> FEATURE:
<221> NAME/KEY: misc_feature
<222> LOCATION: (14)..(14)

<223> OTHER INFORMATION: Lys is glycated
<220> FEATURE:
<221> NAME/KEY: misc_feature
<222> LOCATION: (30)..(30)
<223> OTHER INFORMATION: Lys is glycated
<220> FEATURE:
<221> NAME/KEY: misc_feature
<222> LOCATION: (41)..(41)
<223> OTHER INFORMATION: Lys is glycated
<220> FEATURE:
<221> NAME/KEY: misc_feature
<222> LOCATION: (65)..(66)
<223> OTHER INFORMATION: Lys is glycated
<220> FEATURE:
<221> NAME/KEY: misc_feature
<222> LOCATION: (85)..(85)
<223> OTHER INFORMATION: Lys is glycated

<400> SEQUENCE: 8

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Lys Phe Glu His Cys Asn Phe Asn
        35                  40                  45

Asp Val Thr Thr Arg Leu Arg Glu Asn Glu Leu Thr Tyr Tyr Cys Cys
    50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Val Thr Pro Phe Leu Ala
                85                  90                  95

Ala Ala Trp Ser Leu His Pro
            100

<210> SEQ ID NO 9
<211> LENGTH: 578
<212> TYPE: DNA
<213> ORGANISM: Homo sapiens

<400> SEQUENCE: 9
ctttagcacc agttggtgta ggagttgaga cctacttcac agtagttctg tggacaatca      60
caatgggaat ccaaggaggg tctgtcctgt tcgggctgct gctcgtcctg gctgtcttct     120
gccattcagg tcatagcctg cagtgctaca actgtcctaa cccaactgct gactgcaaaa     180
cagccgtcaa ttgttcatct gattttgatg cgtgtctcat taccaaagct gggttacaag     240
tgtataacaa gtgttggaag tttgagcatt gcaatttcaa cgacgtcaca acccgcttga     300
gggaaaatga gctaacgtac tactgctgca agaaggacct gtgtaacttt aacgaacagc     360
ttgaaaatgg tgggacatcc ttatcagaga aaacagttct tctgctggtg actccatttc     420
tggcagcagc ctggagcctt catccctaag tcaacaccag agagcttcct cccaaactcc     480
ccgttcctgc gtagtccgct ttctcttgct gccacattct aaaggcttga tattttccaa     540
atggatcctg ttgggaaaga ataaaattag cttgagca                             578

<210> SEQ ID NO 10
<211> LENGTH: 14
<212> TYPE: PRT
<213> ORGANISM: Homo sapiens

<400> SEQUENCE: 10

Asn Lys Ala Trp Lys Phe Glu His Ala Asn Phe Asn Asp Cys
1               5                   10

<210> SEQ ID NO 11
<211> LENGTH: 36
<212> TYPE: DNA
<213> ORGANISM: Homo sapiens

<400> SEQUENCE: 11
gtcgttgaaa ttacaatgct caaactgcca acactt   36

<210> SEQ ID NO 12
<211> LENGTH: 27
<212> TYPE: DNA
<213> ORGANISM: Homo sapiens

<400> SEQUENCE: 12
gttgaaattg cactgctcaa acttcca   27

<210> SEQ ID NO 13
<211> LENGTH: 18
<212> TYPE: PRT
<213> ORGANISM: Homo sapiens

<400> SEQUENCE: 13

Trp Lys Phe Glu His Cys Asn Phe Asn Asp Val Thr Thr Arg Leu Arg
1               5                   10                  15

Glu Asn

<210> SEQ ID NO 14
<211> LENGTH: 23
<212> TYPE: PRT
<213> ORGANISM: Homo sapiens

<400> SEQUENCE: 14

Cys Trp Lys Phe Glu His Cys Asn Phe Asn Asp Val Thr Thr Arg Leu
1               5                   10                  15

Arg Glu Asn Glu Leu Thr Tyr
            20

<210> SEQ ID NO 15
<211> LENGTH: 30
<212> TYPE: PRT
<213> ORGANISM: Homo sapiens

<400> SEQUENCE: 15

Ala Gly Leu Gln Val Tyr Asn Lys Cys Trp Lys Phe Glu His Cys Asn
1               5                   10                  15

Phe Asn Asp Val Thr Thr Arg Leu Arg Glu Asn Glu Leu Thr
            20                  25                  30

<210> SEQ ID NO 16
<211> LENGTH: 16
<212> TYPE: PRT
<213> ORGANISM: Homo sapiens

<400> SEQUENCE: 16

Gln Val Tyr Asn Lys Cys Trp Lys Phe Glu His Cys Asn Phe Asn Asp
1               5                   10                  15

<210> SEQ ID NO 17
<211> LENGTH: 17
<212> TYPE: PRT
<213> ORGANISM: Homo sapiens

```
<400> SEQUENCE: 17

Ala Gly Leu Gln Val Tyr Asn Lys Cys Trp Lys Phe Glu His Cys Asn
1               5                   10                  15

Phe

<210> SEQ ID NO 18
<211> LENGTH: 42
<212> TYPE: PRT
<213> ORGANISM: Homo sapiens

<400> SEQUENCE: 18

Asp Phe Asp Ala Cys Leu Ile Thr Lys Ala Gly Leu Gln Val Tyr Asn
1               5                   10                  15

Lys Cys Trp Lys Phe Glu His Cys Asn Phe Asn Asp Val Thr Thr Arg
            20                  25                  30

Leu Arg Glu Asn Glu Leu Thr Tyr Tyr Cys
        35                  40

<210> SEQ ID NO 19
<211> LENGTH: 18
<212> TYPE: PRT
<213> ORGANISM: Homo sapiens

<400> SEQUENCE: 19

Lys Cys Trp Lys Phe Glu His Cys Asn Phe Asn Asp Val Thr Thr Arg
1               5                   10                  15

Leu Arg

<210> SEQ ID NO 20
<211> LENGTH: 26
<212> TYPE: PRT
<213> ORGANISM: Homo sapiens

<400> SEQUENCE: 20

Lys Cys Trp Lys Phe Glu His Cys Asn Phe Asn Asp Val Thr Thr Arg
1               5                   10                  15

Leu Arg Glu Asn Glu Leu Thr Tyr Tyr Cys
            20                  25

<210> SEQ ID NO 21
<211> LENGTH: 13
<212> TYPE: PRT
<213> ORGANISM: Homo sapiens

<400> SEQUENCE: 21

Val Tyr Asn Lys Cys Trp Lys Phe Glu His Cys Asn Phe
1               5                   10

<210> SEQ ID NO 22
<211> LENGTH: 18
<212> TYPE: PRT
<213> ORGANISM: Homo sapiens

<400> SEQUENCE: 22

Gly Leu Gln Val Tyr Asn Lys Cys Trp Lys Phe Glu His Cys Asn Phe
1               5                   10                  15

Asn Asp

<210> SEQ ID NO 23
<211> LENGTH: 14
<212> TYPE: PRT
```

<213> ORGANISM: Homo sapiens

<400> SEQUENCE: 23

Tyr Asn Lys Cys Trp Lys Phe Glu His Cys Asn Phe Asn Glu
1               5                   10

<210> SEQ ID NO 24
<211> LENGTH: 18
<212> TYPE: PRT
<213> ORGANISM: Homo sapiens

<400> SEQUENCE: 24

Ala Gly Leu Gln Val Tyr Asn Lys Cys Trp Lys Phe Glu His Cys Asn
1               5                   10                  15

Phe Asn

<210> SEQ ID NO 25
<211> LENGTH: 9
<212> TYPE: PRT
<213> ORGANISM: Homo sapiens

<400> SEQUENCE: 25

Asn Lys Cys Trp Lys Phe Glu His Cys
1               5

<210> SEQ ID NO 26
<211> LENGTH: 13
<212> TYPE: PRT
<213> ORGANISM: Homo sapiens

<400> SEQUENCE: 26

Pro Asn Pro Thr Ala Asp Cys Lys Thr Ala Val Asn Cys
1               5                   10

<210> SEQ ID NO 27
<211> LENGTH: 8
<212> TYPE: PRT
<213> ORGANISM: Homo sapiens

<400> SEQUENCE: 27

Asp Cys Lys Thr Ala Val Asn Cys
1               5

<210> SEQ ID NO 28
<211> LENGTH: 13
<212> TYPE: PRT
<213> ORGANISM: Homo sapiens

<400> SEQUENCE: 28

Pro Asn Pro Thr Ala Asp Cys Lys Thr Ala Val Asn Cys
1               5                   10

<210> SEQ ID NO 29
<211> LENGTH: 14
<212> TYPE: PRT
<213> ORGANISM: Homo sapiens

<400> SEQUENCE: 29

Leu Gln Cys Tyr Asn Cys Pro Asn Pro Thr Ala Asp Cys Lys
1               5                   10

<210> SEQ ID NO 30
<211> LENGTH: 13
<212> TYPE: PRT

<213> ORGANISM: Homo sapiens

<400> SEQUENCE: 30

Asp Phe Asp Ala Cys Leu Ile Thr Lys Ala Gly Leu Gln
1               5                   10

<210> SEQ ID NO 31
<211> LENGTH: 14
<212> TYPE: PRT
<213> ORGANISM: Homo sapiens

<400> SEQUENCE: 31

Phe Asp Ala Cys Leu Ile Thr Lys Ala Gly Leu Gln Val Tyr
1               5                   10

<210> SEQ ID NO 32
<211> LENGTH: 12
<212> TYPE: PRT
<213> ORGANISM: Homo sapiens

<400> SEQUENCE: 32

Cys Leu Ile Thr Lys Ala Gly Leu Gln Val Tyr Asn
1               5                   10

<210> SEQ ID NO 33
<211> LENGTH: 11
<212> TYPE: PRT
<213> ORGANISM: Homo sapiens

<400> SEQUENCE: 33

Asp Phe Asp Ala Cys Leu Ile Thr Lys Ala Gly
1               5                   10

<210> SEQ ID NO 34
<211> LENGTH: 7
<212> TYPE: PRT
<213> ORGANISM: Homo sapiens

<400> SEQUENCE: 34

Gln Val Tyr Asn Lys Cys Trp
1               5

<210> SEQ ID NO 35
<211> LENGTH: 6
<212> TYPE: PRT
<213> ORGANISM: Homo sapiens

<400> SEQUENCE: 35

Val Tyr Asn Lys Cys Trp
1               5

<210> SEQ ID NO 36
<211> LENGTH: 10
<212> TYPE: PRT
<213> ORGANISM: Homo sapiens

<400> SEQUENCE: 36

Ala Gly Leu Gln Val Tyr Asn Lys Cys Trp
1               5                   10

<210> SEQ ID NO 37
<211> LENGTH: 15
<212> TYPE: PRT
<213> ORGANISM: Homo sapiens -continued

<400> SEQUENCE: 37

Ala Gly Leu Gln Val Tyr Asn Lys Cys Trp Lys Phe Glu His Cys
1               5                   10                  15

<210> SEQ ID NO 38
<211> LENGTH: 16
<212> TYPE: PRT
<213> ORGANISM: Homo sapiens

<400> SEQUENCE: 38

Leu Thr Tyr Tyr Cys Cys Lys Lys Asp Leu Cys Asn Phe Asn Glu Gln
1               5                   10                  15

<210> SEQ ID NO 39
<211> LENGTH: 15
<212> TYPE: PRT
<213> ORGANISM: Homo sapiens

<400> SEQUENCE: 39

Asn Glu Leu Thr Tyr Tyr Cys Cys Lys Lys Asp Leu Cys Asn Phe
1               5                   10                  15

<210> SEQ ID NO 40
<211> LENGTH: 16
<212> TYPE: PRT
<213> ORGANISM: Homo sapiens

<400> SEQUENCE: 40

Leu Arg Glu Asn Glu Leu Thr Tyr Tyr Cys Cys Lys Lys Asp Leu Cys
1               5                   10                  15

<210> SEQ ID NO 41
<211> LENGTH: 25
<212> TYPE: PRT
<213> ORGANISM: Homo sapiens

<400> SEQUENCE: 41

Cys Asn Phe Asn Asp Val Thr Thr Arg Leu Arg Glu Asn Glu Leu Thr
1               5                   10                  15

Tyr Tyr Cys Cys Lys Lys Asp Leu Cys
            20                  25

<210> SEQ ID NO 42
<211> LENGTH: 8
<212> TYPE: PRT
<213> ORGANISM: Homo sapiens

<400> SEQUENCE: 42

Tyr Cys Cys Lys Lys Asp Leu Cys
1               5

<210> SEQ ID NO 43
<211> LENGTH: 19
<212> TYPE: PRT
<213> ORGANISM: Homo sapiens

<400> SEQUENCE: 43

Thr Thr Arg Leu Arg Glu Asn Glu Leu Thr Tyr Tyr Cys Cys Lys Lys
1               5                   10                  15

Asp Leu Cys

<210> SEQ ID NO 44
<211> LENGTH: 21

```
<212> TYPE: PRT
<213> ORGANISM: Homo sapiens

<400> SEQUENCE: 44

Val Thr Thr Arg Leu Arg Glu Asn Glu Leu Thr Tyr Tyr Cys Cys Lys
1               5                   10                  15

Lys Asp Leu Cys Asn
            20

<210> SEQ ID NO 45
<211> LENGTH: 21
<212> TYPE: PRT
<213> ORGANISM: Homo sapiens

<400> SEQUENCE: 45

Phe Asn Asp Val Thr Thr Arg Leu Arg Glu Asn Glu Leu Thr Tyr Tyr
1               5                   10                  15

Cys Cys Lys Lys Asp
            20

<210> SEQ ID NO 46
<211> LENGTH: 16
<212> TYPE: PRT
<213> ORGANISM: Homo sapiens

<400> SEQUENCE: 46

Gly Thr Ser Leu Ser Glu Lys Thr Val Leu Leu Leu Val Thr Pro Phe
1               5                   10                  15

<210> SEQ ID NO 47
<211> LENGTH: 14
<212> TYPE: PRT
<213> ORGANISM: Homo sapiens

<400> SEQUENCE: 47

Leu Ser Glu Lys Thr Val Leu Leu Leu Val Thr Pro Phe Leu
1               5                   10

<210> SEQ ID NO 48
<211> LENGTH: 10
<212> TYPE: PRT
<213> ORGANISM: Homo sapiens

<400> SEQUENCE: 48

Thr Ser Leu Ser Glu Lys Thr Val Leu Leu
1               5                   10

<210> SEQ ID NO 49
<211> LENGTH: 13
<212> TYPE: PRT
<213> ORGANISM: Homo sapiens

<400> SEQUENCE: 49

Leu Glu Asn Gly Gly Thr Ser Leu Ser Glu Lys Thr Val
1               5                   10
```

ANTI-GLYCATED CD59 ANTIBODIES AND USES THEREOF

GOVERNMENT SUPPORT

This invention was made with government support under Grant No. DK052855 and Grant No.: DK062994 awarded by the National Institutes of Health. The United States government may have certain rights in the invention.

FIELD OF THE INVENTION

This invention relates generally to preparation and use of antibodies that specifically recognize glycated epitopes on glycated CD59 polypeptides. In particular, the invention relates in part to antibodies or antigen-binding fragments thereof that bind specifically to glycated CD59.

BACKGROUND OF THE INVENTION

Diabetes Mellitus (diabetes) is a leading cause of morbidity and mortality in the adult population. This is primarily because diabetic patients tend to develop vascular complications that involve the kidneys (diabetic nephropathy), the retina (diabetic retinopathy), as well as large and small blood vessels in other organs (macro- and micro-vascular disease) including nerves (diabetic neuropathy). It is well established that the vascular complications of diabetes are caused by elevated blood glucose levels over long periods of time. Elevated blood glucose levels affect proteins by a process known as glycation. Different "glycated" proteins have been identified in diabetic subjects, including albumin, hemoglobin and others. Measurement of the extent of protein "glycation" of certain proteins is considered a valuable clinical tool to assess long-term glycemic control and thereby the efficacy of diabetes treatment.

Glycation, the non-enzymatic attachment of glucose to proteins, is considered a major pathophysiological mechanism causing tissue damage in diabetic subjects. Glycation involves the reaction of glucose and/or other reducing sugars with amino groups in proteins resulting in the formation of a Schiff base or aldimine. This labile adduct can tautomerize via the Amadori rearrangement to the more stable ketoamine. The function of the glycated protein may be impaired, depending on the location of the amino group(s) affected. For example, amino-terminal glycation of the β-chains of hemoglobin gives rise to the glycated hemoglobins (HbA1) in which responsiveness to 2,3-diphosphoglycerate is decreased and oxygen affinity increased. Glycation of the major thrombin inhibitor of the coagulation system, antithrombin III, decreases its affinity for heparin, and has been postulated to contribute to the hypercoagulable state associated with diabetes.

Hemoglobin glycation and thrombin inhibitor glycation do not account for the vascular complications of diabetes. The mechanism which results in such complications remains unknown.

Currently, protein glycation in diabetic subjects is measured in blood by estimating the amount of glycated hemoglobin (hemoglobin A1c) through a complicated clinical test that requires extraction of a blood sample. Accordingly, there is a need for a simplified and less invasive method for rapid monitoring of protein glycation levels.

SUMMARY OF THE INVENTION

The present invention relates to antibodies or antigen-binding fragments thereof which specifically bind glycated CD59 polypeptide, compositions containing one or a combination of such antibodies or antigen-binding fragments thereof, hybridoma cell lines that produce the antibodies, and methods of making and using the antibodies or antigen-binding fragments thereof for diagnosis and treatment of diabetic and related conditions.

The invention disclosed herein describes novel methods of producing an antibody that specifically binds glycated CD59 protein. The invention also includes in some aspects the use of an antibody that specifically binds to glycated CD59. In some embodiments, the glycated CD59 of the invention is K41-glycated CD59. The invention also includes in some aspects immunogenic glycated CD59, including fragments thereof, that may be used to prepare an antibody that specifically binds glycated CD59. The invention also includes in some aspects, methods of preparing an immunogenic glycated CD59 polypeptide and compositions for detecting and measuring glycated CD59 levels, particularly as they relate to glycemic levels. The discovery of an antibody that specifically binds to glycated CD59 facilitates analysis of diseases in which the amount of CD59 glycation differs from normal levels. For example, it has been discovered that the level of glycation of CD59 is elevated in diabetes. Thus, onset, progression and/or regression of diabetes or other diseases can be monitored by monitoring levels of glycated CD59 in a subject. It also has been determined, surprisingly, that CD59 is present in urine, saliva, tissue, etc. Therefore, the measurement can be done in urine or other samples without requiring a blood sample.

According to one aspect of the invention, isolated antibodies or antigen-binding fragments thereof are provided. The antibodies or antigen-binding fragments thereof bind specifically to a glycated epitope of glycated CD59, wherein the epitope includes a glycated lysine. In some embodiments, the glycated lysine is K41 of CD59. In certain embodiments, the epitope includes K41-glycated WKFEH (SEQ ID NO:1). In some embodiments, the antibody or antigen-binding fragment thereof binds to a conformational epitope. In some embodiments the antibody is clone 7. In some embodiments, the antibody is a monoclonal antibody. In some embodiments, the antibody is a recombinant antibody. In some embodiments, the antibody is a polyclonal antibody. In some embodiments, the antibody or antigen-binding fragment is attached to a detectible label. In some embodiments, the detectible label is selected from the group consisting of a fluorescent label, an enzyme label, a radioactive label, a nuclear magnetic resonance active label, a luminescent label, and a chromophore label. In certain embodiments, the antibody or antigen-binding fragment thereof is lyophilized. In certain embodiments, the antibody or antigen-binding fragment thereof is in an aqueous medium.

According to another aspect of the invention, an isolated nucleic acid sequence is provided. The nucleic acid sequence encodes an antibody of any of the foregoing aspects of the invention. The invention also includes in some aspects, hybridomas that include one of the foregoing nucleic acid sequences of the invention. According to another aspect of the invention, a hybridoma cell line that produces an antibody of a forgoing aspect of the invention is provided. According to another aspect of the invention, an expression vector that includes an isolated nucleic acid molecule encoding the antibody or antigen-binding fragment thereof of a foregoing aspect of the invention is provided. In some embodiments, the invention includes a host cell transformed by or transfected with the expression vector. In certain embodiments, the invention includes a plasmid which produces an antibody or antigen-binding fragment thereof of any of the forgoing aspects of the invention.

According to another aspect of the invention, a nucleic acid sequence that encodes the antibody clone 7 is provided. In some aspects of the invention a hybridoma is provided that includes the nucleic acid that encodes clone 7. According to another aspect of the invention, a hybridoma that produces the antibody clone 7 is provided.

According to another aspect of the invention, an expression vector is provided that includes an isolated nucleic acid molecule encoding antibody clone 7 or an antigen-binding fragment thereof. In some embodiments, a host cell transformed by or transfected with the expression vector.

According to yet another aspect of the invention, an isolated antibody or an antigen-binding fragment that specifically glycated CD59 is provided and the antibody or the antigen-binding fragment thereof competitively inhibits the binding of clone 7 to glycated CD59.

According to another aspect of the invention, kits for detecting the presence of glycated CD59 are provided. The kits include a package including a container containing the isolated antibody or antigen-binding fragment thereof of any of the aforementioned aspects of the invention, and instructions for use of the antibody or antigen-binding fragment thereof to detect the presence of glycated CD59. In some embodiments, the antibody is clone 7. In certain embodiments, the antibody is a monoclonal antibody. In some embodiments, the antibody is a recombinant antibody. In certain embodiments, the antibody is a polyclonal antibody. In some embodiments, the antibody or antigen-binding fragment thereof is attached to a detectible label. In certain embodiments, the detectible label is selected from the group consisting of a fluorescent label, an enzyme label, a radioactive label, a nuclear magnetic resonance active label, a luminescent label, and a chromophore label. In some embodiments, the antibody or antigen-binding fragment thereof is lyophilized. In certain embodiments, the antibody or antigen-binding fragment thereof is packaged in an aqueous medium. In some embodiments, the kit also includes a container containing a second antibody or antigen-binding fragment thereof that specifically binds non-glycated CD59 or non-K41-glycated CD59, and instructions for using the second antibody as a control antibody. In some embodiments, the control is a positive control.

According to yet another aspect of the invention, kits are provided that include a package including a container containing a hybridoma that comprises a nucleic acid sequence that encodes an antibody of any of the foregoing aspects of the invention and instructions for producing the antibody. In some embodiments, the hybridoma includes the nucleic acid sequence that encodes the antibody clone 7.

According to another aspect of the invention, kits are provided that include a package comprising a container containing an expression vector comprising an isolated nucleic acid molecule encoding antibody clone 7 or an antigen-binding fragment thereof.

According to another aspect of the invention, immunogenic polypeptides are provided. The immunogenic polypeptides include the amino acid sequence set forth as WKFEH (SEQ ID NO:2), and the amino acid sequence of the polypeptide is a modified amino acid sequence of SEQ ID NO:5 or fragment thereof wherein the modification of the amino acid sequence set forth as SEQ ID NO:5 is the presence of one or more glucocytol-lysine residues, or the replacement of one or more cysteine residues with alanine residues, or the addition of a cysteine residue to the C-terminus, or combinations thereof. In some embodiments, the amino acid sequence of the immunogenic polypeptide is set forth as SEQ ID NO:3.

According to yet another aspect of the invention, methods of making antibodies that specifically bind to glycated CD59 but not to nonglycated CD59 are provided. The methods include preparing an immunogenic polypeptide of any of the foregoing aspects of the invention, and immunizing an animal with the immunogenic polypeptide. In some embodiments, the methods also include removing a lymph node from the immunized animal, harvesting cells from the removed lymph node, fusing the harvested cells with mouse myeloma cells to make hybridomas, expanding the hybridomas, identifying a hybridoma that produces an antibody that specifically binds to an immunogenic polypeptide of one of the foregoing aspects of the invention and collecting the antibody produced by the hybridoma. In some embodiments of the foregoing aspects of the invention, the animal is a mouse. In some embodiments of the foregoing aspects of the invention, the myeloma cells are AG8 cells. In some embodiments of the foregoing aspects of the invention, the immunogenic polypeptide has the amino acid sequence set forth as SEQ ID NO:3.

These and other aspects of the invention will be described in further detail in connection with the detailed description of the invention.

BRIEF DESCRIPTION OF THE DRAWINGS

FIG. 7A shows that the anti-glycated CD59 antibody recognizes purified human CD59 after (lane 2) but not before glycation (lane 1) and does not recognize another glycated protein such as glycated albumin (lane 3). FIG. 7B shows the OD readings in an ELISA which indicate that the anti-glycated CD59 antibody preferentially recognizes glycated CD59 and not non-glycated CD59 or albumen.

FIG. 4 is representative of experiments run three times with comparable results. Inset shows the number of CD59 molecules incorporated per GPE as determined with $^{125}$I-CD59 before (C) and after (R) glycation with ribose.

FIG. 5A is a digitized image of a western blot and FIGS. 5B and 5C are graphs. Panel (5A) indicates expression of wild-type (WT) CD59, and CD59 mutants Gln-41 and Gln-44 in CHO cells as confirmed by SDS-PAGE followed by Western blot analysis of CHO cell extracts using the YTH 53.1 monoclonal antibody, Vector (closed square); WT (open square); CD59-Gln-41 (open triangle); Gln-44 (open circle). Panel (5B) indicates activity of WT and mutant CD59s tested in the GPE hemolytic assay before and after glycation with ribose for the time intervals indicated. Panel (5C) indicates CD59 and mutant CD59 activity as a percent of control activity for a cell suspension of GPE incubated with purified WT CD59

Figure 1:
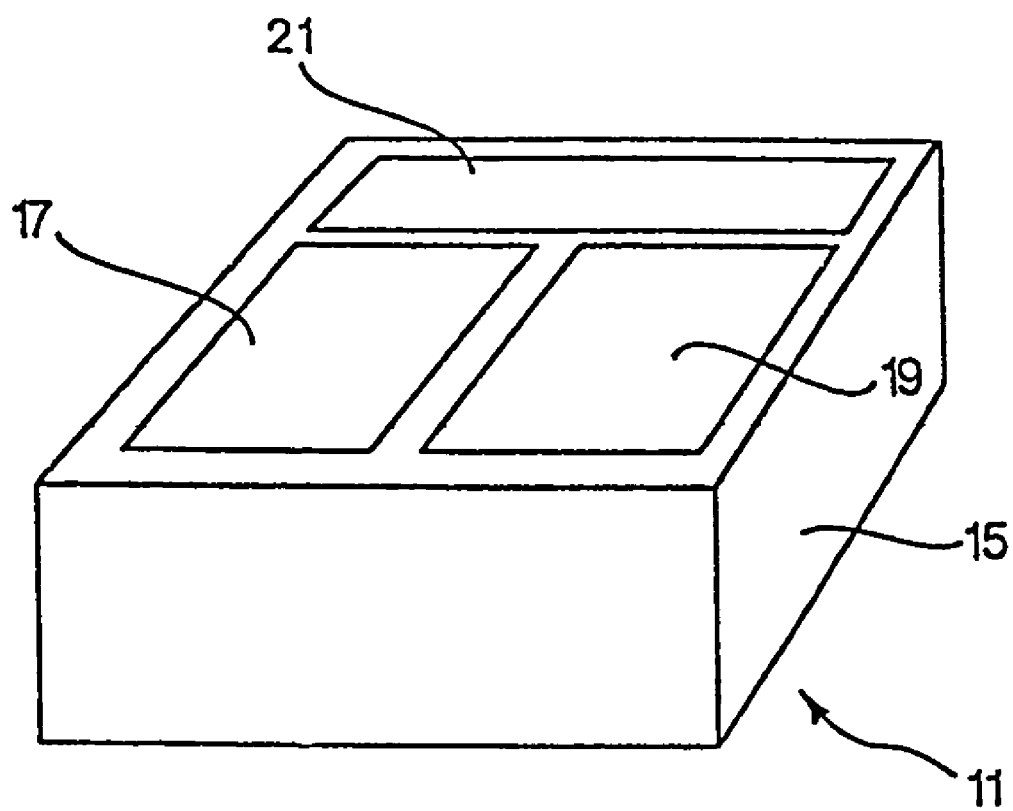
FIG. 1 depicts a schematic of a kit according to the invention.

(open squares) and Gln-41 (open triangles), and Gln-44 (open circles) following incubation with the glycating sugar ribose. Data points represent the mean of triplicate determinations (SEM are smaller than the data points). The figure is representative of experiments run three times with comparable results.

FIGS. 6A and 6B are bar graphs. Panel (6A) is a bar graph indicating HUVEC incubated with or without 50 mM ribose followed by reduction with cyanoborohydride. Cells were then exposed to purified terminal complement components C5b6, C7, C8 and C9 to form the MAC and the mitogenic activity in the conditioned medium was measured. Results are expressed as the ratio of mitogenic activity released into the conditioned media in the presence or absence of MAC. Panel (6B) indicates Human RBC incubated without or with 50 mM ribose followed by reduction with cyanoborohydride to stabilize labile Schiff base adducts. After volume adjustment, aliquots of glycated and non glycated cells were separated for rescue with purified CD59 (4 μg), exposure to neutralizing anti-CD59 antibody (YTH53.1) or both, and then exposed to purified C5b6, C7, C8 and C9 to form the MAC. Open columns represent control cells not exposed to cyanoborohydride, filled columns represent cells exposed to cyanoborohydride, as above.

FIGS. 7A and 7B are images of immunoblots. Panel (7A) is an immunoblot of urine samples from non-diabetic (lanes 1, 4 and 5) and diabetic (lanes 2 and 3) subjects. Urine was concentrated by ultrafiltration, separated by anion exchange chromatography and fractions dot-blotted for the presence of CD59 with anti-CD59 specific antibody. CD59-positive fractions were pooled and immunoprecipited with the HC1 anti-CD59 specific antibody. The immunoprecipitate was separated by SDS-PAGE and immunoblotted. Panel (7A), upper blot: immunoblot of CD59 positive fractions of the immunoprecipitate with the monoclonal anti-CD59 YTH53.1. Lower blot: The immunoprecipitate separated by SDS-PAGE and immunoblotted with the anti-hexitol-lysine antibody. Lower section, Panel A indicates levels of glycated CD59 and glycated hemoglobin (HbA1c). Panel (7B). Immunoblot of glycated (G) and non-glycated (NG) albumin (left) and affinity chromatography purified CD59 (right) with anti-hexitol-lysine antibody.

DETAILED DESCRIPTION OF THE INVENTION

The present invention provides antibodies or antigen-binding fragments thereof which bind specifically to glycated CD59 polypeptide, compositions containing one or a combination of such antibodies or antigen-binding fragments thereof, hybridoma cell lines that produce the antibodies, and methods of making and using the antibodies or antigen-binding fragments thereof for diagnosis and treatment of diabetic conditions and diabetes-related conditions. In contrast to markers of glycation such as hemoglobin, glycation of CD59 is believed to be involved in the pathogenesis of the vascular complications of diabetes. Accordingly, clinical evaluation of glycated CD59 is a more direct measure for vascular complications of diabetes induced by glycation.

As used herein, CD59 (also known as membrane inhibitor of reactive lysis [MIRL], protectin, HRF20 and H19) and glycated CD59 are a polypeptide having essentially the amino acid sequence identity of Accession No. M95708 (Davies, A., et al., *Journal J. Exp. Med.* 170 (3), 637-654 (1989)). A nucleic acid sequence encoding CD59 also is provided by Davis, A, et al. A CD59 sequence is provided herein as SEQ ID NO:5, which represents non-glycated CD59. The sequence of non-glycated CD59 that is present in mature form in cells and tissues is set forth as SEQ ID NO:6. The sequence of mature CD59 that is glycated at. K41 is set forth as SEQ ID NO:7. The sequence of mature CD59 that is glycated at K14, K30, K38, K41, K65, K66, and K85 is set forth as SEQ ID NO:8.

As used herein, "glycated CD59" means CD59 that has been glycated. In some embodiments, glycated CD59 is CD59 that has been glycated at the amino acid residue that corresponds to the amino acid residue number 41 of full-length mature CD59, which is set forth herein as SEQ ID NO:6. The residue in position 41 of full-length mature CD59 is a lysine, and this lysine in the full length and the residue that corresponds to this position in fragments is referred to herein as "K41". CD59 in which the K41 residue is glycated is referred to herein as K41-glycated CD59. In some embodiments, a glycated lysine residue is a glycocytol-lysine residue. Thus, a glycated CD59 or fragment thereof may be glycated by the inclusion of a glycocytol-lysine residue. In certain embodiments, a lysine residue of CD59 or a fragment thereof may be glycated by contacting the CD59 or fragment thereof with glycating sugars (e.g. glucose, ribose, or glycose-6-phosphate).

It is known that the CD59 polypeptide sequence includes a 25 amino acid signal peptide that is cleaved when CD59 is produced, thus forming the mature CD59 protein sequence. As would be understood by one of ordinary skill in the art, CD59 in a sample obtained from a subject would be CD59 from which the signal peptide has been cleaved. The sequence of the CD59 polypeptide prior to removal of the signal peptide is provided herein as SEQ ID NO:5 and the amino acid sequence of mature CD59 polypeptide is set forth herein as SEQ ID NO:6.

We have determined, surprisingly, that glycation of CD59, including, but not limited to K41 glycation of CD59, is correlated to abnormal blood sugar levels and that glycation of CD59 interferes with the normal activity of CD59. CD59 functions normally by binding to the terminal components of the membrane attack complex of complement (MAC), thereby interfering with membrane insertion and polymerization of the C9 component of complement. Glycation at the K41 of CD59 interferes with CD59's ability to prevent the assembly of the MAC. While not wishing to be bound by any theory, it is believed that, as a result of glycation of CD59, the MAC is permitted to be activated and leads to the development of proliferative chronic diabetic complications. Indeed, the present inventor has shown that the membrane attack complex stimulates proliferation of fibroblasts, smooth muscle, mesangial and other cells, in part by releasing growth factors such as FGF and PDGF from MAC-targeted-endothelium. The MAC also induces increased synthesis of extracellular matrix proteins by mesangial cells. Thus, increased MAC deposition in diabetic tissues is believed to induce growth factor release from endothelium, which stimulates cell proliferation in the vascular wall and contributes to the expansion of the extracellular matrix and to the glomerulosclerosis that characterizes diabetic nephropathy.

The invention includes in one aspect, methods and compositions for the preparation of antibodies that specifically bind glycated CD59. Compositions useful for making an antibody of the invention include a glycated CD59 polypeptide molecule. As used herein, a glycated CD59 polypeptide or fragment thereof means a glycated full-length CD59 polypeptide, or a fragment of a full-length CD59 that is a glycated fragment. One such glycated CD59 polypeptide that is useful in the methods of the invention is the polypeptide set forth as NH$_2$-NKAWKFEHANFNDC (SEQ ID NO:3) In SEQ ID NO:3, the lysine (K) that is residue 5 of SEQ ID NO:3 corresponds to the lysine that is residue 41 (K41) of the mature CD59 polypeptide sequence, and in SEQ ID NO:3, the K5 residue is glycated.

The invention also involves fragments of the foregoing proteins. A fragment of K41-glycated CD59 comprises at least 8, 9, 10, 11, 12, 13, 14, 15, 16, 17, 18, 19 or 20 or more contiguous amino acids of CD59 having a consecutive sequence found in CD59 or a modified CD59 sequence as described herein. In some embodiments, a fragment includes K41, which may or may not be glycated K41. Fragments of glycated CD59 can be used for a variety of purposes, including in the preparation of molecules that bind specifically to glycated CD59 and in immunoassays well known to those of ordinary skill in the art, including competitive binding immunoassays.

The methods of the invention include methods to make an antibody that specifically binds to a glycated CD59 polypeptide. As used herein, the term "glycated CD59" polypeptide includes mature CD59 polypeptide with one or more glycated lysine (K) residues. In some embodiments, the glycated lysine residue of CD59 is residue K41 of mature CD59. One of ordinary skill in the art will understand that a fragment of CD59 can be compared to mature full-length CD59, and the presence of a residue in that fragment is said to "correspond" to the residue of mature CD59. As used herein therefore, residue positions for lysines are identified as they occur in mature CD59, whether that residue is part of mature CD59 or part of a fragment or modified fragment. Thus, K41 maintains that designation in mature CD59 or fragments thereof. In some embodiments, the glycated lysine residue in a fragment of CD59 is K41. In certain embodiments of the invention, the glycated residue of CD59 or a fragment thereof is or corresponds to K14, K30, K38, K65, K66, or K85 of mature CD59 polypeptide. In some embodiments, more than one K residue is glycated.

The methods of the invention include the use of an immunogenic polypeptide for the production of an anti-glycated CD59 antibody. In some embodiments, an antigenic polypeptide can be as small as 5 amino acids in length. For example, WKFEH (SEQ ID NO:1) is an antigenic fragment that may be used to generate antibodies that specifically recognize glycated CD59. In some embodiments, when the size of the polypeptide is less than about 8 amino acids in length, a second carrier molecule, e.g. bovine serum albumin (BSA), may be attached to the peptide to increase antigenicity of the polypeptide. Thus, small fragments of CD59 that include the desired epitope for antibody production can be used in the production of an antibody that specifically binds to the epitope. As set forth herein, SEQ ID NO:2 is WKFEH, wherein the K residue is not glycated.

In one embodiment, antibodies that bind specifically WKFEH (SEQ ID NO:1), are provided. For example, the antibody clone 7 specifically binds to the glycated WKFEH epitope. In the preparation of antibodies that specifically bind to glycated CD59, WKFEH (SEQ ID NO:1) can be used. SEQ ID NO:1 can be used in conjunction with a second molecule, e.g. BSA as described above, as an antigenic polypeptide with which to prepare antibodies that specifically bind to the WKFEH (SEQ ID NO:1) epitope. In addition, one or more amino acids that correspond to amino acids of CD59 or a modified CD59 as described herein can be added to either or both ends of the WKFEH (SEQ ID NO:1) sequence to make additional immunogenic polypeptides for use in making an antibody of the invention. For example, one or more amino acids may be added to the N-terminal end and/or one or more amino acids may be added to the C-terminal end of SEQ ID:1 for the production of an immunogenic fragment useful in the methods of the invention. It will be understood that 1, 2, 3, 4, 5, 6, 7, 8, 9, 10, 11, 12, 13, 14, 15, 16, 17, 18, 19, 20, or more amino acids that correspond to an amino acid of CD59 or a modified CD59 as described herein can be added to one or both ends of the amino acid sequence of WKFEH (SEQ ID NO:1). Therefore, an immunogenic fragment of the invention may include WKFEH (SEQ ID NO:1) with from 1 to 39 amino acids that correspond to amino acids of CD59 or a modified CD59 as described herein added to the N-terminal end and/or from 1 to 59 amino acids that correspond to amino acids of CD59 or a modified CD59 as described herein added to the C-terminal end. Examples of fragments that include K41, although not intended to be limiting are WKFEHCNFNDVTTRLREN (SEQ ID NO:13); CWKFEHCNFNDVTTRLRENELTY (SEQ ID NO:14); AGLQVYNKCWKFEHCNFNDVTTRLRENELT (SEQ ID NO:15); QVYNKCWKFEHCNFND (SEQ ID NO:16); AGLQVYNKCWKFEHCNF (SEQ ID NO:17); DFDACLITKAGLQVYNKCWKFEHCNFNDVTTRLRENELTYYC (SEQ ID NO:18); KCWKFEHCNFNDVTTRLR (SEQ ID NO:19); KCWKFEHCNFNDVTTRLRENELTYYC (SEQ ID NO:20); VYNKCWKFEHCNF (SEQ ID NO:21); GLQVYNKCWKFEHCNFND (SEQ ID NO:22); YNKCWKFEHCNFNE (SEQ ID NO:23); AGLQVYNKCWKFEHCNFN (SEQ ID NO:24); and NKCWKFEHC (SEQ ID NO:25). In some embodiments, the fragment is a K14-glycated fragment.

The invention also includes fragments of CD59 that include a lysine that is K14, K30, K38, K65, K66, or K85. In some embodiments of the invention the lysine is glycated and in some embodiments of the invention the lysine is not glycated. In one embodiments, a fragment of CD59 that is useful in the invention is at least five amino acids in length and includes K14, with between 1 and 13 amino acids that correspond to amino acids of CD59 or a modified CD59 as described herein added to the N-terminal side and/or from 1 to 89 amino acids that correspond to amino acids of CD59 or a modified CD59 as described herein added to the C-terminal side. Examples of fragments that include K14, although not intended to be limiting are: PNPTADCKTAVNC (SEQ ID NO:26); DCKTAVNC (SEQ ID NO:27); PNPTADCKTAVNC (SEQ ID NO:28); and LQCYNCPNPTADCK (SEQ ID NO:29). In some embodiments, the fragment is a K14-glycated fragment.

Another fragment of CD59 that is useful in the invention is at least five amino acids in length and includes K30, with between 1 and 29 amino acids that correspond to amino acids of CD59 or a modified CD59 as described herein added to the N-terminal side and/or from 1 to 73 amino acids that correspond to amino acids of CD59 or a modified CD59 as described herein added to the C-terminal side. Examples of fragments that include K30, although not intended to be limiting are: DFDACLITKAGLQ (SEQ ID NO:30); FDACLITKAGLQVY (SEQ ID NO:31); CLITKAGLQVYN (SEQ ID NO:32); and DFDACLITKAG (SEQ ID NO:33). In some embodiments, the fragment is a K30-glycated fragment.

Another fragment of CD59 that is useful in the invention is at least five amino acids in length and includes K38, with between 1 and 37 amino acids that correspond to amino acids of CD59 or a modified CD59 as described herein added to the N-terminal side and/or from 1 to 65 amino acids that correspond to amino acids of CD59 or a modified CD59 as described herein added to the C-terminal side. Examples of fragments that include K38, although not intended to be limiting are: QVYNKCW (SEQ ID NO:34); VYNKCW (SEQ ID NO:35); AGLQVYNKCW (SEQ ID NO:36); and AGLQVYNKCWKFEHC (SEQ ID NO:37). In some embodiments, the fragment is a K38-glycated fragment.

Another fragment of CD59 that is useful in the invention is at least five amino acids in length and includes K65, with between 1 and 64 amino acids that correspond to amino acids of CD59 or a modified CD59 as described herein added to the N-terminal side and/or from 1 to 38 amino acids that correspond to amino acids of CD59 or a modified CD59 as described herein added to the C-terminal side. A fragment of CD59 that is useful in the invention is at least five amino acids in length and includes K66, with between 1 and 65 amino acids that correspond to amino acids of CD59 or a modified CD59 as described herein added to the N-terminal side and/or from 1 to 37 amino acids that correspond to amino acids of CD59 or a modified CD59 as described herein added to the C-terminal side. Examples of fragments that include K65 and K66, although not intended to be limiting are: LTYYCCK-KDLCNFNEQ (SEQ ID NO:38); NELTYYCCKKDLCNF (SEQ ID NO:39); LRENELTYYCCKKDLC (SEQ ID NO:40); CNFNDVTTRLRENELTYYCCKKDLC (SEQ ID NO:41); YCCKKDLC (SEQ ID NO:42); TTRLRENELTYY-CCKKDLC (SEQ ID NO:43); VTTRLRENELTYYCCK-KDLCN (SEQ ID NO:44); and FNDVTTRLRENELTYYC-CKKD (SEQ ID NO:45). In some embodiments, the fragment is a K65- and/or a K66-glycated fragment.

Another fragment of CD59 that is useful in the invention is at least five amino acids in length and includes K85, with between 1 and 84 amino acids that correspond to amino acids of CD59 or a modified CD59 as described herein added to the N-terminal side and/or from 1 to 18 amino acids that correspond to amino acids of CD59 or a modified CD59 as described herein added to the C-terminal side. Examples of fragments that include K85, although not intended to be limiting are: GTSLSEKTVLLLVTPF (SEQ ID NO:46); LSEK-TVLLLVTPFL (SEQ ID NO:47); TSLSEKTVLL (SEQ ID NO:48); and LENGGTSLSEKTV (SEQ ID NO:49). In some embodiments, the fragment is a K85-glycated fragment.

It will be understood by those of ordinary skill in the art that it is preferable that a fragment of CD59 for use as an immunogenic fragment in the methods of the invention be at least 5, 6, 7, 8, 9, 10, 11, 12, 13, 14, 15, 16, 17, 18, 19, 20 or more amino acids in length. If a fragment of CD59 includes more than one lysine residue, it is desirable that in some embodiments, only one of the lysine residues is a glycated lysine residue. One of ordinary skill in the art will be able to use the guidance provided herein to make additional fragments of CD59 that can be used in the methods of the invention.

An amino acid sequence for use in methods of the invention to produce an antibody that specifically binds to glycated CD59 can be modified in one or more ways. Modifications of the amino acids sequence means substituting one or more lysine residues with glycocytol-lysine, substituting of one or more cysteine residues with alanine residues, and/or adding a cysteine residue to the C-terminus. An example of a fragment of CD59 that can be modified is NKCWKFEHCNFND (SEQ ID NO:4). SEQ ID NO:4 may be modified to include a glycocytol-lysine residue in place of the K in residue position 5 of the sequence. In addition, the cysteine residues in positions 3 and 9 of SEQ ID NO:4 can be replaced with alanine residues, to reduce S-S bridging in the polypeptide. Further, a cysteine residue may be added to the C-terminus of SEQ ID NO:4 to create a "handle" for solid phase purification of the synthesized polypeptide. The resulting modified polypeptide fragment of CD59 is set forth as NKAWKFEHANFNDC (SEQ ID NO:3), and is useful in the antibody-production methods of the invention. One of ordinary skill in the art will recognize that there are additional polypeptide fragments of CD59 that can be used and/or modified and used in the methods of the invention. Thus, the invention includes polypeptides with an epitope of interest, e.g. WKFEH (SEQ ID NO:1) that may be flanked on either or both sides with one or more additional amino acids that correspond to an amino acid sequence of CD59 and may include modifications from the amino acid sequence of CD59 as described herein.

As used herein with respect to polypeptides, proteins or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

Fragments of a CD59 protein preferably are those fragments that retain a distinct functional capability of the CD59 protein. Functional capabilities which can be retained in a fragment include interaction with antibodies, and interaction with other polypeptides or fragments thereof. Other CD59 protein fragments, e.g., recombinant fragments of SEQ ID NO:5, can be selected. For example, one of ordinary skill in the art can prepare CD59 fragments recombinantly and test those fragments according to the methods exemplified below.

Modifications to a CD59 polypeptide may be made by modification of the nucleic acid which encodes the CD59 polypeptide may include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the CD59 amino acid sequence.

In general, modified CD59 polypeptides include polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a CD59 polypeptide by eliminating proteolysis by proteases in an expression system (e.g., dibasic amino acid residues in yeast expression systems in which KEX2 protease activity is present).

Modifications conveniently are prepared by altering a nucleic acid molecule that encodes the CD59 polypeptide. Mutations of a nucleic acid which encode a CD59 polypeptide preferably preserve the amino acid reading frame of the coding sequence, and preferably do not create regions in the nucleic acid which are likely to hybridize to form secondary structures, such a hairpins or loops, which can be deleterious to expression of the modified polypeptide.

Modifications can be made by selecting an amino acid substitution, or by random mutagenesis of a selected site in a nucleic acid which encodes the CD59 polypeptide. Modified CD59 polypeptides then can be expressed and tested for one or more activities (e.g., antibody binding) to determine which mutation provides a modified polypeptide with the desired properties. Further mutations can be made to modified CD59 polypeptides (or to non-modified CD59 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a CD59 coding sequence or cDNA clone to enhance expression of the polypeptide. The activity of modified CD59 polypeptides can be tested by cloning the gene encoding the modified CD59 polypeptide into a bacterial or mammalian expression vector, introducing the vector into an appropriate host cell, expressing the modified CD59 polypeptide, and testing for functional capability of CD59 polypeptides as disclosed herein. The foregoing procedures are well known to one of ordinary skill in the art.

The skilled artisan will also realize that conservative amino acid substitutions may be made in CD59 polypeptides to provide functionally equivalent CD59 polypeptides, i.e., modified CD59 polypeptides that retain the functional capabilities of CD59 polypeptides. As used herein, a "conservative amino acid substitution" refers to an amino acid substitution which does not alter the relative charge or size characteristics of the protein in which the amino acid substitution is made. Modified CD59 polypeptides can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent CD59 polypeptides include conservative amino acid substitutions of SEQ ID NO:5, or fragments thereof, such as a recombinant CD59 polypeptide. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in CD59 polypeptides typically are made by alteration of a nucleic acid encoding a CD59 polypeptide. Such substitutions can be made by a variety of methods known to one of ordinary skill in the art. For example, amino acid substitutions may be made by PCR-directed mutation, site-directed mutagenesis, or by chemical synthesis of a gene encoding a CD59 polypeptide. Where amino acid substitutions. are made to a small fragment of a CD59 polypeptide, the substitutions can be made by directly synthesizing the peptide. The activity of finctionally equivalent fragments of CD59 polypeptides can be tested by cloning the gene encoding the altered CD59 polypeptide into a bacterial or mammalian expression vector, introducing the vector into an appropriate host cell, expressing the altered CD59 polypeptide, and testing for a functional capability of the CD59 polypeptides as disclosed herein.

The methods of the invention include the use of polypeptide fragments of CD59 for the production of antibodies that specifically bind to glycated CD59. In some embodiments, the glycated residue on CD59 that is part of the epitope specifically recognized by the antibody is the lysine residue that corresponds to K41 of CD59. The invention also includes nucleic acid sequences that encode the polypeptide sequences of the invention. For example, the invention includes nucleic acid sequences that encode a CD59 polypeptide or fragment thereof, and includes the use of the nucleic acid sequences for the production of the polypeptide sequences. The full-length nucleic acid sequence of CD59 is set forth herein as SEQ ID NO:9. Fragments of SEQ ID NO:9 that encode polypeptides of CD59 that can be used to produce antibodies that recognize glycated CD59 are useful in methods of the invention.

Additional nucleic acids of the invention include nucleic acids that encode an antibody or antigen-binding fragment thereof of the invention. In certain embodiments, a nucleic acid of the invention is a nucleic acid molecule that is highly homologous to a nucleic acid that encodes an antibody or antigen-binding fragment thereof of the invention. Preferably the homologous nucleic acid molecule comprises a nucleotide sequence that is at least about 90% identical to the nucleotide sequence that encodes the antibody or antigen-binding fragment thereof. More preferably, the nucleotide sequence is at least about 95% identical, at least about 97% identical, at least about 98% identical, or at least about 99% identical to a nucleotide sequence that encodes an antibody or antigen-binding fragment thereof of the invention. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus the invention also includes antibodies having the glycated CD59-binding properties and other fimctional properties described herein, which are encoded by nucleic acid molecules that hybridize under high stringency conditions to a nucleic acid that encodes an antibody or antigen-binding fragment thereof of the invention. Identification of related sequences can also be achieved using polymerase chain reaction (PCR) and other amplification techniques suitable for cloning related nucleic acid sequences. Preferably, PCR primers are selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen (e.g., glycated CD59). In some embodiments, the glycated CD59 is K41-glycated CD59. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al, (1989) *Nature* 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

As used herein, "specific binding" refers to antibody binding to a predetermined antigen with a preference that enables the antibody to be used to distinguish the antigen from others to an extent that permits the diagnostic assays described herein. Specific binding to glycated CD59 means that the antibody not only preferentially binds CD59 versus other proteins, but also that it preferentially binds a glycated CD59 molecule versus one that is not glycated. Typically, the antibody binds with an affinity that is at least two-fold greater than its affinity for binding to a antigens other than the predetermined antigen. In some embodiments, an antibody or antigen-binding fragment thereof of the invention specifically binds to K41-glycated CD59 and in other embodiments an antibody of the invention or antigen-binding fragment thereof specifically binds to a CD59 that is glycated at lysine residue that does not correspond to K41 of CD59.

The isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g. IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, and a Fv fragment.

The antibodies of the present invention can be polyclonal, monoclonal, or a mixture of polyclonal and monoclonal antibodies. The antibodies can be produced by a variety of techniques well known in the art. An example of a method to produce a monoclonal antibody that specifically binds K41-glycated CD59 is provided in the Examples section and is discussed further below. In some embodiments, the epitope recognized by a monoclonal antibody of the invention includes glycated lysine that corresponds to the K41 in mature CD59. In some embodiments, the epitope recognized by a monoclonal antibody of the invention includes WKFEH (SEQ ID NO:1).

Monoclonal antibody production may be effected by techniques described in the Examples section and by using alternative methods that are known in the art. The Examples section provides methods of producing a monoclonal antibody that specifically binds to K41-glycated CD59. The term "monoclonal antibody," as used herein, refers to a preparation of antibody molecules of single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide, e.g., with glycated CD59 or a fragment thereof, or K41-glycated CD59 or a fragment thereof in the present invention. In some embodiments, the polypeptide is a modified polypeptide as described herein. In some embodiments the polypeptide comprises the sequence set forth as SEQ ID NO:1. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rabbit, hamster, sheep and frog may also be used as hosts for preparing antibody-producing cells. See; Goding (in Monoclonal Antibodies: Principles and Practice, 2d ed., pp. 60-61, Orlando, Fla., Academic Press, 1986). Mouse strains that have human immunoglobulin genes inserted in the genome (and which cannot produce mouse immunoglobulins) can also be used. Examples include the HuMAb mouse strains produced by Medarex/GenPharm International, and the XenoMouse strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include Ag8, P3-X63/Ag8, X63-Ag8.653, NS1/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elsevier, 1984).

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference).

Procedures for raising polyclonal antibodies are well known to those of ordinary skill in the art. For example anti-glycated CD59 polyclonal antibodies may be raised by administering glycated CD59 protein subcutaneously to New Zealand white rabbits which have first been bled to obtain pre-immune serum. The glycated CD59 can be injected at a total volume of 100 µl per site at six different sites, typically with one or more adjustments. The rabbits are then bled two weeks after the first injection and periodically boosted with the same antigen three times every six weeks. A sample of serum is collected 10 days after each boost. Polyclonal antibodies are recovered from the serum, preferably by affinity chromatography using glycated CD59 to capture the antibody. This and other procedures for raising polyclonal antibodies are disclosed in E. Harlow, et al., editors, Antibodies: A Laboratory Manual (1988), which is hereby incorporated by reference. In some embodiments, the epitope recognized by the polyclonal antibody includes glycated lysine that corresponds to the K41 in mature CD59. In some embodiments, the epitope recognized by the polyclonal antibody includes WKFEH (SEQ ID NO:1).

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

The present invention further provides nucleic acid molecules encoding anti-glycated CD59 antibodies (e.g. anti-K41-glycated CD59 antibodies) and vectors comprising the nucleic acid molecules as described herein. The vectors provided can be used to transform or transfect host cells for producing anti-glycated CD59 antibodies with the specificity of antibodies described herein. In an important embodiment the antibodies produced will have the specificity of the antibody clone 7. In one embodiment, the vectors can comprise an isolated nucleic acid molecule encoding a heavy chain and/or a light chain of an antibody of the invention encoded by a nucleic acid molecule. In a further embodiment, plasmids are given which produce the antibodies or antigen-binding fragments described herein.

In some aspects of the invention, the antibody or antigen-binding fragment thereof binds to a conformational epitope within the glycated CD59 molecule. To determine if the selected anti-glycated CD59 antibodies bind to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibodies bind conformational epitopes. Antibodies that bind to native protein but not denatured protein are those antibodies that bind conformational epitopes, and are preferred antibodies.

In some embodiments, antibodies of the invention competitively inhibit the specific binding of a second antibody to its target glycated epitope on glycated CD59. In some embodiments, the target epitope includes the sequence set forth as WKFEH (SEQ ID NO:1), which is glycated. In one embodiments, the second antibody is clone 7. To determine competitive inhibition, a variety of assays known to one of ordinary skill in the art can be employed. For example, competition assays can be used to determine if an antibody competitively inhibits binding to glycated CD59 (or K41-glycated CD59) by another antibody. These methods may include cell-based methods employing flow cytometry or solid phase binding analysis. Other assays that evaluate the ability of antibodies to cross-compete for glycated CD59 (or K41-glycated CD59) molecules in solid phase or in solution phase, also can be used.

Certain antibodies competitively inhibit the specific binding of a second antibody to its target epitope on glycated CD59 (or K41-glycated CD59) by at least about 10%, 20%, 30%, 40%, 50%, 60%, 70%, 80%, 90%, 95%, or 99%. Inhibition can be assessed at various molar ratios or mass ratios; for example competitive binding experiments can be conducted with a 2-fold, 3-fold, 4-fold, 5-fold, 7-fold, 10-fold or more molar excess of the first antibody over the second antibody.

Other antibodies include antibodies that specifically bind to an epitope on glycated CD59 defined by a second antibody. To determine the epitope, one can use standard epitope mapping methods known in the art. For example, fragments (peptides) of K41-glycated CD59 antigen (preferably synthetic peptides) that bind the second antibody can be used to determine whether a candidate antibody binds the same epitope. In some embodiments, the epitope is WKFEH (SEQ ID NO:1), which includes the glycated K that corresponds to K41 of mature CD59. In one embodiment, the second antibody is clone 7. For linear epitopes, overlapping peptides of a defined length (e.g., 8 or more amino acids) are synthesized. The peptides preferably are offset by 1 amino acid, such that a series of peptides covering every 8 amino acid fragment of the glycated CD59 protein sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies can be determined using standard methodologies including surface plasmon resonance (BIACORE) and ELISA assays. For examination of conformational epitopes, larger glycated CD59 fragments, including in some embodiments K41-glycated CD59, can be used. Other methods that use mass spectrometry to define conformational epitopes have been described and can be used (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of *Current Protocols in Immunology*, Coligan et al., eds., John Wiley & Sons. Epitopes can be confirmed by introducing point mutations or deletions into a known epitope, and then testing binding with one or more antibodies to determine which mutations reduce binding of the antibodies.

An antibody or antigen-binding fragment thereof of the invention can be linked to a detectable label. Detectible labels useful in the invention include, but are not limited to: a fluorescent label, an enzyme label, a radioactive label, a nuclear magnetic resonance active label, a luminescent label, and a chromophore label. The detectible labels of the invention can be attached to the antibodies or antigen-binding fragments thereof by standard protocols known in the art. In some embodiments, the detectible labels may be covalently attached to an anti-CD59 antibody or antigen-binding fragment thereof of the invention. The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In some embodiments, it is contemplated that one may wish to first derivatize the antibody, and then attach the detectible label to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene. In some embodiments, a radionuclide may be coupled to an antibody or antigen-binding fragment thereof by chelation.

The compositions (antibodies to glycated CD59 and derivatives/conjugates thereof) of the present invention have diagnostic and therapeutic utilities. For example, these molecules can be administered to cells in culture, e.g. in vitro or ex vivo, or to a sample obtained from a subject to diagnose a variety of disorders. As detailed herein, the antibodies or antigen-binding fragments thereof of the invention may be used for example to isolate and identify CD59 protein and/or glycated and/or nonglycated CD59 protein. The antibodies may be coupled to specific diagnostic labeling agents for imaging of the protein or fragment thereof. The antibodies or antigen-binding fragments thereof of the invention may also be used for immunoprecipitation, immunoblotting CD59 and/or glycated CD59 using standard methods known to those of ordinary skill in the art.

The invention in some aspects includes various assays to determine the levels of glycated CD59. The methods of the invention that are useful to determine levels of glycated CD59 in cells, tissues, and samples from subjects, include, but are not limited to: binding assays, such as described in the examples below; specific binding assays, such as using antibodies or antigen-binding fragments thereof of the invention that bind specifically to glycated CD59; gel electrophoresis; mass spectrometry; NMR; and the like. Immunoassays may be used according to the invention including sandwich-type assays, competitive binding assays, one-step direct tests and two-step tests such as described in the examples.

The methods and assays of the invention (e.g. binding assays, gel electrophoresis; mass spectrometry; NMR; and the like) may be used to monitor changes in blood sugar levels in a subject over time. Thus, the methods of the invention may be used to examine changes in glycated CD59 levels in a subject over time. This allows monitoring of glycated CD59 levels in a subject who is believed to be at risk of developing a diabetic condition and also enables monitoring in a subject who is known to have a diabetic condition. Thus, the methods of the invention may be used to assess the efficacy of a therapeutic treatment of a diabetic condition by the assessment of the level of glycated CD59 in a subject at various time points. For example, a level of a subject's glycated CD59 can be obtained prior to the start of a therapeutic regimen (either prophylactic or as a treatment of an existing diabetic condition), during the treatment regimen and/or after a treatment regimen, thus providing information on the effectiveness of the regimen in the patient.

It will be understood that a therapeutic regimen may be either prophylactic or a treatment of an existing diabetic condition in a subject. Thus, the methods of the invention may be used to monitor a subject's response to prophylactic therapy and/or treatment for a diabetic condition provided to a subject. Thus, the methods of the invention (e.g. binding assays, gel electrophoresis; mass spectrometry; NMR; and the like) may also be useful to monitor the progression or regression of a diabetic condition in a subject. The level of glycated CD59 may be determined in two, three, four, or more samples obtained from a subject over time. The level of glycated CD59 in the samples may be compared and changes in the levels over time may be used to assess glycemic control in the subject.

One aspect of the present invention relates to the use of the antibodies and/or antigen-binding fragments thereof of the invention for detecting glycated CD59 proteins or portions thereof in a biological sample (e.g., histological or cytological specimens, body fluid samples, biopsies and the like), and, in particular, to distinguish the level of glycated CD59 from the level of non-glycated CD59 in a sample or a subject. This method involves providing an antibody or an antigen-binding binding fragment thereof, which specifically binds to glycated CD59, e.g., clone 7 or other anti-glycated CD59 antibody. The anti-CD59 antibody may be bound to a label that permits the detection of the glycated CD59. The biological sample is contacted with the labeled anti-glycated CD59 antibody under conditions effective to permit binding of the anti-glycated CD59 antibody to glycated CD59 in the sample. The presence of glycated CD59 in the biological sample is detected by detection of the label. In one preferred form, the contact between the anti-glycated CD59 antibody and the biological sample is carried out in samples from a subject. Samples to which the methods of the invention can be applied include tissue and body fluid samples.

Thus, the anti-glycated CD59 antibodies of the present invention can be used in immunofluorescence techniques to examine human tissue, cell and bodily fluid specimens. In some embodiments, the samples are fresh samples. In some embodiments, slides containing cryostat sections of frozen, unfixed tissue biopsy samples or cytological smears are air dried, formalin or acetone fixed, and incubated with the monoclonal antibody preparation in a humidified chamber at room temperature. The slides are then washed and further incubated with a preparation of a secondary antibody directed against the monoclonal antibody, usually some type of anti-mouse immunoglobulin if the monoclonal antibodies used are derived from the fusion of a mouse spleen lymphocyte and a mouse myeloma cell line. This secondary antibody is tagged with a compound, for instance rhodamine or fluorescein isothiocyanate, that fluoresces at a particular wavelength. The staining pattern and intensities within the sample are then determined by fluorescent light microscopy and optionally photographically recorded.

As yet another alternative, computer enhanced fluorescence image analysis or flow cytometry can be used to examine tissue specimens or cells using the anti-glycated CD59 antibodies of the invention. The anti-glycated CD59 antibodies of the invention are particularly useful in assessing samples obtained from subjects which can be evaluated using a fluorescence image analyzer or with a flow cytometer.

The antibodies and/or antigen-binding fragments thereof of the present invention can be used to screen patients for diseases associated with the presence of elevated levels of glycated CD59. As used herein, the term "elevated" means higher, for example elevated versus a control level. In addition, the antibodies of the invention can be used to identify the recurrence of such diseases. The antibodies of the invention are particularly useful in assays to differentiate whether or not a subject has a diabetic condition, because the glycated CD59 protein to which the anti-glycated CD59 antibodies bind is present in increased amounts in tissues and body fluids of subjects who have a diabetic condition. The percent of glycated CD59 in a sample can be used to determine the presence and/or status of a diabetic condition. The antibodies of the invention can be used to obtain useful prognostic information by providing an early indicator of disease onset and /or progression.

In some embodiments of the invention, the antibodies of the present invention can be used in combination with other known antibodies to provide additional information regarding the level of glycated CD59 as a percentage of the level of total CD59 in a sample. For example, an antibody that binds CD59 (glycated and non-glycated) can be used to determine the total amount or level of CD59 in a sample, can be used in conjunction with an antibody of the invention that specifically binds a glycated CD59 to determine a percentage of total CD59 in a sample that is glycated CD59.

The step of contacting an antibody or antigen-binding fragment thereof of the invention with a sample to be tested can be carried out in a sample of saliva, urine, serum or other body fluids, to detect the presence of glycated CD59 in the body fluid. When the contacting is carried out in a saliva, urine, or serum sample, it is preferred that the antibody or antigen-binding fragment thereof of the invention recognize substantially no antigens in the sample other than glycated CD59. In some embodiments, it is preferred that the antibody or antigen-binding fragment thereof of the invention recognize substantially no antigens in the sample other than K41-glycated CD59.

Antibodies and antigen-binding fragments thereof suitable for detecting glycated CD59 include anti-glycated CD59 antibodies, such as monoclonal or polyclonal antibodies. In addition, antibody fragments, half-antibodies, hybrid derivatives, probes, and other molecular constructs may be utilized. In some embodiments, the antibodies are anti-K41-glycated CD59 antibodies.

The antibodies or antigen-binding fragments thereof of the invention may also be used in a variety of assays based upon detecting levels of glycated CD59 in subjects. The assays include (1) characterizing the impact of blood sugar levels on glycation levels in a subject; (2) evaluating a treatment for regulating blood sugar levels in a subject; (3) selecting a treatment for regulating blood sugar levels in a subject; and (4) determining progression, progression or onset of a condition characterized by abnormal levels of glycated protein in a subject. Thus, subjects can be characterized, treatment regimens can be monitored, treatments can be selected and diseases can be better understood using the assays of the present invention. For example, the antibodies or antigen-binding fragments thereof of the invention are useful in one aspect in methods for measuring the level of glycated CD59 in a subject, which is a direct indicator of the level of the subject's glycemic control. The impact of blood sugar levels or glycation levels thus can be measured due to the positive correlation between the level of circulating blood glucose and the amount of glycation of endogenous CD59. The level of glycated CD59 thus correlates with the level of glycemic control in the subject. Relatively low levels of glycated CD59 reflect well-controlled circulating blood sugar levels and selectively high levels of glycated CD59 reflect poorly controlled glycemic levels.

The antibodies or antigen-binding fragments thereof of the invention may be used in assays described herein, which are carried out on samples obtained from subjects. As used herein, a subject is a human, non-human primate, cow, horse, pig, sheep, goat, dog, cat, or rodent. In all embodiments, human subjects are preferred. The samples used herein are any body tissue or body fluid sample obtained from a subject. Preferred are body fluids, for example, lymph, saliva, blood, urine, and the like. Saliva, blood and urine are preferred, saliva and urine being most preferred. It has been surprisingly discovered that glycated CD59 can be detected in saliva and urine, thereby obviating the need for a blood sample.

Particularly, important subjects to which the present invention can be applied are diabetic subjects.

The term "diabetic" as used herein, means an individual who, at the time the sample is taken, has a primary deficiency of insulin and/or an abnormal (e.g. reduced) ability to metabolize glucose, e.g. impaired glucose tolerance versus a normal subject. The term diabetic includes, but is not limited to, individuals with juvenile diabetes (Type 1 diabetes), adult-onset diabetes (Type 2 diabetes), gestational diabetes, and any other conditions of insulin deficiency or reduction in the ability to metabolize glucose. The term "diabetic" is a term of art, known and understood by those practicing in the medical profession, a formal definition of which can be found in Harrison's Principles of Medicine (Harrisons, Vol 14, Principles of Internal Medicine, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

All of the assays described herein may include the use of the antibodies or antigen-binding fragments thereof of the invention and involve measuring levels of glycated CD59. Levels of glycated CD59 can be determined in a number of ways when carrying out the various methods of the invention. In one particularly important measurement, the level of glycated CD59 is measured in relation to nonglycated CD59. Thus, the measurement is a relative measure, which can be expressed, for example, as a percentage of total CD59. Another measurement of the level of glycated CD59 is a measurement of absolute levels of glycated CD59. This could be expressed, for example, in terms of grams per liter of body fluid. Another measurement of the level of glycated CD59 is a measurement of the change in the level of glycated CD59 over time. This may be expressed in an absolute amount or may be expressed in terms of a percentage increase or decrease over time. The antibodies or antigen-binding fragments of the invention may be used in diagnostic methods alone or in conjunction with certain antibodies already known in the art. The known antibodies may include anti-CD59 antibodies as well as anti-glycation-moiety antibodies, for example, Anti-CD-59 YTH53.1, and the anti-hexitol-lysine antibody, which binds to glycated CD59. Various examples of the use of known antibodies in the methods of the invention are provided in the Example section.

Importantly, levels of glycated CD59 can be determined using the antibodies or antigen-binding fragments thereof of the invention and are advantageously compared to controls according to the invention. The control may be a predetermined value, which can take a variety of forms. It can be a single cut-off value, such as a median or mean. It can be established based upon comparative groups, such as in groups having normal amounts of circulating insulin and groups having abnormal amounts of circulating insulin. Another example of comparative groups would be groups having a particular disease, condition or symptoms and groups without the disease, condition or symptoms. Another comparative group would be a group with a family history of a condition and a group without such a family history. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or amounts of glycated protein and the highest quandrant or quintile being individuals with the highest risk or amounts of glycated protein.

The predetermined value, of course, will depend upon the particular population selected. For example, an apparently healthy population will have a different 'normal' range than will a population which is known to have a condition related to abnormal protein glycation. Accordingly, the predetermined value selected may take into account the category in which an individual falls. Appropriate ranges and categories can be selected with no more than routine experimentation by those of ordinary skill in the art. As used herein, "abnormal" means not normal as compared to a control. By abnormally high it is meant high relative to a selected control. Typically the control will be based on apparently healthy normal individuals in an appropriate age bracket.

In measuring the relative amount of glycated CD59 to nonglycated CD59, those of ordinary skill in the art will appreciate that the relative amount may be determined by measuring either the relative amount of glycated CD59 or the relative amount of nonglycated CD59. In other words, if 90% of an individual's CD59 is nonglycated CD59, then 10% of the individual's CD59 will be glycated CD59. Thus, measuring the level of glycated CD59 may be carried out using an antibody or antigen-binding fragment thereof of the invention in methods to measure the relative amount of nonglycated CD59.

It will also be understood that the controls according to the invention may be, in addition to predetermined values, samples of materials tested in parallel with the experimental materials. Examples include samples from control populations or control samples generated through manufacture to be tested in parallel with the experimental samples.

The invention includes various assays used to determine the levels of glycated CD59 and include: binding assays, such as described in the examples below; specific binding assays, such as using antibodies or antigen-binding fragments thereof of the invention that bind specifically to glycated CD59; gel electrophoresis; mass spectrometry; NMR; and the like. Immunoassays may be used according to the invention including sandwich-type assays, competitive binding assays, one-step direct tests and two-step tests such as described in the examples.

As mentioned above, it is also possible to use the antibodies or antigen-binding fragments thereof of the invention to characterize blood sugar levels by monitoring changes in the absolute or relative amounts of glycated CD59 over time. For example, it is expected that an increase in glycated CD59 correlates with increasing dysregulation of glycemic levels. Accordingly one can monitor glycated CD59 levels over time to determine if glycemic levels of a subject are changing. Changes in relative or absolute glycated CD59 of greater than 0.1% may indicate an abnormality. Preferably, the change in glycated CD59 levels, which indicates an abnormality, is greater than 0.2%, greater than 0.5%, greater than 1.0%, 2.0%, 3.0%, 4.0%, 5.0%, 7.0%, 10%, 15%, 20%, 25%, 30%, 40%, 50%, or more. Reductions in amounts of glycated CD59 over time may indicate improved glycemic control.

The antibodies or antigen-binding fragments thereof of the invention may also be used in diagnostic methods to determine the effectiveness of treatments for abnormal glycemic levels. The "evaluation of treatment" as used herein, means the comparison of a subject's levels of glycated CD59 measured in samples collected from the subject at different sample times, preferably at least one day apart. The preferred time to obtain the second sample from the subject is at least one day after obtaining the first sample, which means the second sample is obtained at any time following the day of the first sample collection, preferably at least 12, 18, 24, 36, 48 or more hours after the time of first sample collection.

The antibodies or antigen-binding fragments thereof of the invention may be used to allow the comparison of levels of glycated CD59 in two or more samples, taken on different days, which is a measure of level of the subject's glycemic control and allows evaluation of the treatment to regulate blood sugar levels. The comparison of a subject's levels of glycated CD59 measured in samples obtained on different days provides a measure of glycemic control to determine the effectiveness of any treatment to regulate blood sugar levels.

As will be appreciated by those of ordinary skill in the art, the evaluation of the treatment also may be based upon an evaluation of the symptoms or clinical end-points of the associated disease, such as the vascular complications of diabetes. Thus, the antibodies or antigen-binding fragments thereof of the invention are useful for determining the regression, progression or onset of a condition which is characterized by abnormal levels of glycated protein, including those characterized by abnormal levels of glycated CD59. In some instances, the antibodies or antigen-binding fragments thereof of the invention can be used to test glycemic control in subjects to which the methods of the invention are applied are already diagnosed as having a particular condition or disease. In other instances, the antibodies or antigen-binding fragments thereof of the invention can be used to obtain measurements that represent the diagnosis of the condition or disease. In some instances, the subjects will already be undergoing drug therapy for regulating blood sugar levels, while in other instances the subjects will be without present drug therapy for regulating blood sugar levels.

According to still another aspect of the invention, the antibodies or antigen-binding fragments thereof of the invention can be used in methods for treating a subject to reduce the risk of a disorder associated with abnormally-high levels of glycated CD59. The method involves selecting and administering to a subject who is known to have an abnormally-high level of glycated CD59, an agent for treating the disorder. Preferably, the agent is an agent for reducing glycated CD59 levels and is administered in an amount effective to reduce glycated CD59 levels.

In this aspect of the invention, the treatments are based upon selecting subjects who have unwanted, elevated levels of glycated CD59, which can be done using the antibodies or antigen-binding fragments thereof of the invention. Such subjects may already be receiving a drug for regulating blood sugar levels, but, according to the invention, are now candidates for an elevated level of the drug based upon the presence of the elevated levels of glycated CD59. It may be appropriate according to the invention to alter a therapeutic regimen for a subject, based upon the measurement of the level of glycated CD59. This can be understood in connection with treatment of diabetics. Diabetics are treated in at least three different ways. Some diabetics are treated only with non-drug therapy, such as exercise and diet. Other diabetics are treated with oral drug therapy, but not with insulin which is injected. Finally, some diabetics are treated with insulin or analogs of insulin by injection. According to the present invention, as a result of determining an elevated level of glycated CD59, an individual undergoing only non-drug therapy may be a candidate for drug therapy as a result of the glycated CD59 test. Likewise, a subject receiving only oral drug therapy, may be a candidate for an insulin-based injectable therapy, due to testing with the antibodies or antigen-binding fragments thereof of the invention to determine levels of glycated CD59. Finally, a subject may be free of any present treatment but may be a candidate for blood sugar level regulating treatment as a result of the use of the antibodies or antigen-binding fragments thereof of the invention in a test for glycated CD59. Thus, subjects may be selected and treated with elevated levels of the same drugs or with different therapies as a result of assays that utilize the antibodies or antigen-binding fragments thereof of the invention.

According to the present invention, some of the subjects are free of symptoms otherwise calling for treatment with a particular therapy. This means that absent the use of the antibodies or antigen-binding fragments thereof of the invention to assess glycated CD59, the subject would not according to convention as of the date of the filing of the present application have symptoms calling for treatment with a particular therapy. It is only as a result of the measuring the level of glycated CD59 that the subject becomes a candidate for treatment with the therapy.

Drug therapies for regulating blood sugar levels include oral therapies with hypoglycemic agents an/or oral anti-diabetic agents, injectable therapies, and the like. Non-drug therapies for regulating blood sugar level include, but are not limited to, dietetic and/or exercise control measures. Diet and exercise alterations include, but are not limited to, reducing caloric intake, and/or increasing fiber intake, and/or decreasing fat intake, and/or increasing exercise level.

Oral drug therapies for regulating blood sugar levels include hypoglycemic agents that may include, but are not limited to:

Acarbose; Acetohexamide; Chlorpropamide; Darglitazone Sodium: Glimepiride; Glipizide; Glyburide, Repaglinide; Troglitazone; Tolazamide; Tolbutamide.

Oral drug therapies for regulating blood sugar levels include antidiabetic agents that may include but are not limited to: Acarbose, Acetohexamide; Buformin; Butoxamine Hydrochloride; Camiglibose; Chlorpropamide; Ciglitazone; Englitazone Sodium; Etoformin Hydrochloride; Gliamilide; Glibomuride; Glicetanile Gliclazide Sodium; Gliflumide; Glipizide; Glucagon; Glyburide; Glyhexamide; Glymidine Sodium; Glyoctamide; Glyparamide; Insulin; Insulin, Dalanated; Insulin Human; Insulin Human, Isophane; Insulin Human Zinc; Insulin Human Zinc, Extended; Insulin, Isophane; Insulin Lispro; Insulin, Neutral; Insulin Zinc; Insulin Zinc, Extended; Insulin Zinc, Prompt; Linogliride; Linogliride Fumarate; Metformin; Methyl Palmoxirate; Palmoxirate Sodium; Pioglitazone Hydrochloride; Pirogliride Tartrate; Proinsulin Human; Repaglinide; Seglitide Acetate; Tolazamide; Tolbutamide; Tolpyrramide; Troglitazone; Zopolrestat.

Injectable therapies for regulating blood sugar levels include, but are not limited to:

Fast-Acting Insulin:

Insulin Injection: regular insulin; Prompt Insulin Zinc Suspension; Semilente® insulin. These categories include preparations such as: Humalog® Injection; Humulin® R; Iletin II; Novolin R, Purified Pork Regular Insulin; Velosulin BR Human Insulin Intermediate-acting Insulin:

Isophane Insulin Suspension: NPH insulin, isophane insulin; Insulin Zinc Suspension Lente® Insulin. These categories include preparations such as: Humulin® L; Humulin® R; Humulin® N NPH; Iletin® II, Lente®; Iletin® II, NPH; Novolin® L, Novolin® N, Purified Pork Lente® insulin, Purified Pork NPH isophane insulin.

Intermediate and Rapid -acting Insulin Combinations:

Human Insulin Isophane Suspension/Human Insulin Injection;. This category includes preparations such as: Humulin® 50/50; Humulin®70/30; Novolin®70/30

Long-acting Insulin:

Protamine Zinc Insulin Suspension; Extended Insulin Zinc Suspension. These categories include preparations such as: Ultralente® Insulin, Humulin® U.

Reducing the risk of a disorder associated with abnormally high levels of glycated CD59 means using treatments and/or medications to reduce glycated CD59 levels, therein reducing, for example, the subject's risk of vascular complications including but not limited to: diabetic nephropathy, diabetic retinopathy, macro-vascular disease, micro-vascular disease, and diabetic neuropathy.

In a subject determined to have an abnormally high level of glycated CD59, an effective amount is that amount effective to reduce glycated CD59 levels in the subject. A response can, for example, also be measured by determining the physiological effects of the hypoglycemic, antidiabetic, or insulin composition, such as the decrease of disease symptoms following administration of the hypoglycemic, antidiabetic, or insulin. Other assays will be known to one of ordinary skill in the art and can be employed for measuring the level of the response. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormally elevated levels of glycated CD59.

An "effective amount" of a drug therapy is that amount of a hypoglycemic, antidiabetic, or insulin or insulin analog that alone, or together with further doses, produces the desired response, e.g. reduction of glycemic level or glycated CD59 levels.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the hypoglycemic, antidiabetic, or insulin composition (alone or in combination with other therapeutic agents) be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of hypoglycemic, antidiabetic, or insulin for producing the desired response in a unit of weight or volume suitable for administration to a patient.

The doses of hypoglycemic, antidiabetic, or insulin administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Various modes of administration will be known to one of ordinary skill in the art which effectively deliver the hypoglycemic, antidiabetic, or insulin to a desired tissue, cell or bodily fluid. Preferred methods for administering the hypoglycemic and antidiabetic are oral. The preferred method of administering insulin is by injection. Administration includes: topical, intravenous, oral, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences*, 18th edition, 1990) provide modes of administration and formulations for delivery of various pharmaceutical preparations and formulations in pharmaceutical carriers. Other protocols which are useful for the administration of hypoglycemic, antidiabetic, or insulin will be known to one of ordinary skill in the art, in which the dose amount, schedule of administration, sites of administration, mode of administration (e.g., intra-organ) and the like vary from those presented herein.

Administration of hypoglycemic, antidiabetic, or insulin to mammals other than humans, e.g. for testing purposes or veterinary therapeutic purposes, is carried out under substantially the same conditions as described above. It will be understood by one of ordinary skill in the art that this invention is applicable to both human and animal diseases which can be treated by hypoglycemic, antidiabetic or insulin. Thus this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the hypoglycemic, antidiabetic, or insulin compositions of the invention.

A hypoglycemic, antidiabetic, or insulin composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the hypoglycemic, antidiabetic, or insulin, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds.

The pharmaceutical compositions also may contain, optionally, suitable preservatives, such as: benzalkonium chloride; chlorobutanol; parabens and thimerosal. The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise hypoglycemic, antidiabetic, or insulin. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

The application of the invention to a diabetic subject under treatment with an oral blood sugar regulating agent and otherwise free of symptoms calling for any oral blood sugar regulating agent, as used herein means a subject treated with oral blood sugar regulators whose glycemic-control levels appear normal based on standard diagnostic criteria, including but not limited to measurement of glycated hemoglobin levels.

The application of the invention to a diabetic subject under treatment with insulin (including analogs thereof) and otherwise free of symptoms calling for any insulin, as used herein means a subject treated with insulin whose glycemic-control levels appear to be normal based on standard diagnostic criteria, including but not limited to measurement of glycated hemoglobin levels.

Dosages of blood sugar regulating agents are well-known to those of ordinary skill in the art and documented in the literature.

Also within the scope of the invention are kits comprising the compositions of the invention and instructions for use. The kits can further contain at least one additional reagent, such as one or more additional antibodies of the invention (e.g., an antibody having a complementary activity which binds to an epitope in glycated CD59 epitope distinct from the first antibody).

Kits containing the antibodies or antigen-binding fragments thereof of the invention can be prepared for in vitro diagnosis, prognosis and/or monitoring a diabetic condition or complication by the immunohistological, immunocytological and immunoserological methods described above. The components of the kits can be packaged either in aqueous medium or in lyophilized form. When the antibodies or antigen-binding fragments thereof are used in the kits in the form of conjugates in which a label moiety is attached, such as an enzyme or a radioactive metal ion, the components of such conjugates can be supplied either in fully conjugated form, in the form of intermediates or as separate moieties to be conjugated by the user or the kit.

A kit may comprise a carrier being compartmentalized to receive in close confinement therein one or more container means or series of container means such as test tubes, vials, flasks, bottles, syringes, or the like. A first of said container means or series of container means may contain one or more anti-glycated CD59 antibodies or antigen-binding fragments thereof or glycated CD59. A second container means or series of container means may contain a label or linker-label intermediate capable of binding to the primary anti-glycated CD59 antibodies (or fragment thereof).

Referring to FIG. 1, a kit according to the invention is shown. The kit 11 includes a package 15 housing a container 17 which contains an agent for determining the level of—glycated CD59 in a sample. The kit also includes a control 19. The kit also may further comprise instructions 21, as described above. The instructions typically will be in written form and will provide guidance for carrying-out the assay embodied by the kit and for making a determination based upon that assay.

Antibodies and antigen-binding fragments of the invention may also be useful in methods of screening for candidate agents that modulate levels of glycated CD59. The methods can include mixing the candidate agent with cells or tissues or in a subject and using the antibodies of the invention to determine the level of glycated CD59 before and after contact with the candidate agent. A decrease in the amount of glycated CD59 formed in comparison to a control is indicative of an agent capable of reducing the production of glycated CD59. An increase in the amount of product formed in comparison to a control is indicative of an agent capable of enhancing the production of glycated CD59.

The assay mixture comprises a candidate agent. The candidate agent is preferably an antibody, a small organic compound, or a peptide, and accordingly can be selected from combinatorial antibody libraries, combinatorial protein libraries, or small organic molecule libraries. Typically, a plurality of reaction mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds, proteins or antibodies (and fragments thereof that bind antigen). In some preferred embodiments, the candidate agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random peptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of and/or the level of glycated CD59 is detected by any convenient method available to the user. For example, the level of glycated CD59 can be determined through the measure of a detectible label. A wide variety of labels can be used, such as those that provide direct detection (e.g., radioactivity, luminescence, optical, or electron density, etc) or indirect detection (e.g., epitope tag such as the FLAG epitope, enzyme tag such as horseradish peroxidase, etc.). The label may be bound to the substrate, or incorporated into the structure of the substrate.

A variety of methods may be used to detect the label, depending on the nature of the label and other assay components. For example, the label may be detected while bound to the substrate or subsequent to separation from the substrate. Labels may be directly detected through optical or electron density, radioactive emissions, nonradiative energy transfers, etc. or indirectly detected with antibody conjugates, strepavidin-biotin conjugates, etc. Methods for detecting a variety of labels are well known in the art.

EXAMPLES

Example 1

Generation of Anti-glycated Human CD59 Monoclonal Antibodies

Introduction

The following procedures were utilized to produce an anti-glycated CD59 specific monoclonal antibody.

Methods

Antigen Production

The immunogen utilized was a 14 amino acid peptide that encompasses the glycation motif K41-H44 of human CD59. The peptide sequence used was:

Relative residue in the whole CD59 protein

```
                                                (SEQ ID NO:3)
50 49 48 47 46 45 44 43 42 41  40 39 38 37
 C  D  N  F  N  A  H  E  F K*   W  A  K N-NH2
14 13 12 11 10  9  8  7  6  5   4  3  2  1
```

Relative residue in the peptide

Because the peptide contains two lysine residues but only one lysine (K*, corresponding to the K41 in the human CD59 protein) is to be glycated, we avoided exposure of the whole peptide to glucose by synthesizing the peptide using a pre-glycated lysine (glucocytol-lysine) for attachment to the peptide structure in the desired position (K5 in the peptide; equivalent to K41 in the whole protein; hereafter referred to as K41).

The glucose attached to the lysine residue for this purpose was a penta-acetate-glucose in which the OH groups were protected with acetate residues to avoid reactivity during the synthesis.

Two cysteine residues in the original CD59 sequence (positions 39 and 45 in the whole protein, 3 and 9 in the peptide) were replaced by alanine to avoid S-S bridging between the cysteine residues. A cysteine residue was added to the C-terminus of the peptide to create a "handle" for solid phase purification of the synthesized peptide. f-moc solid phase peptide synthesis was then carried out following standard procedures. After synthesis and purification, the acetate residues protecting the glucose molecule attached to the K41 residue were removed by incubation at high pH (NaOH).

A non-glycated peptide of identical structure was synthesized in parallel using lysine (instead of glucocytol-lysine) for position K41.

Figure 2:
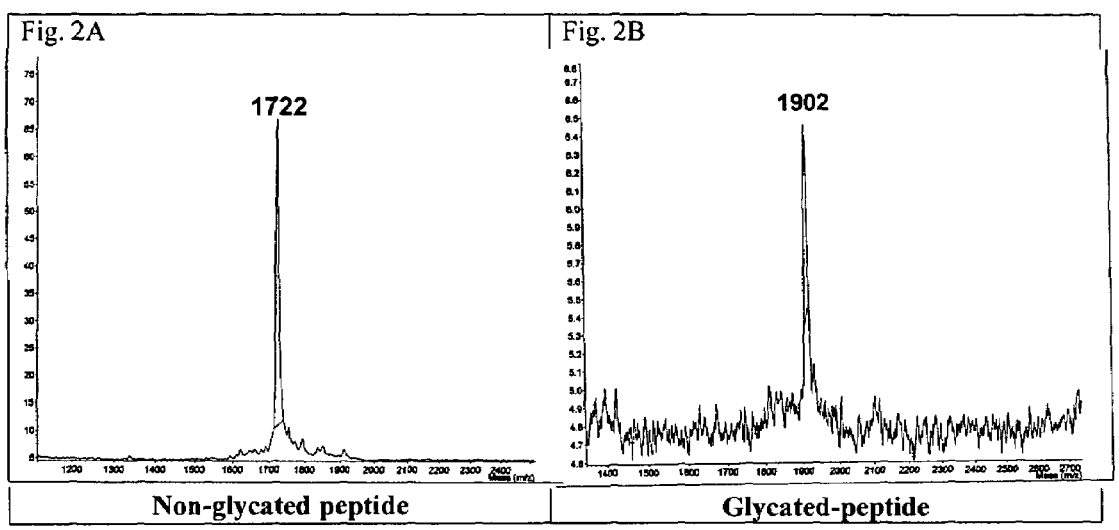
FIG. 2 shows graphs of results of mass spectrometry analysis of both the non-glycated (FIG. 2A) and glycated (FIG. 2B) peptide, the sequences of which are provided herein as SEQ ID NO:4 and SEQ ID NO:3 respectively.

We utilized assessed the glycated and non-glycated peptides using mass spectrometry analysis. FIG. 2 shows results of the mass spectrometry analysis of both the (FIG. 2A) glycated and (FIG. 2B) non-glycated peptides. It illustrates the difference of ≈180 mass units corresponding to the molecular weight of glucose.

Antibody Production

For production of the antibody, we used popliteal lymph node lymphocytes instead of spleen lymphocytes for fusion with mouse myeloma AG8 cells.

Materials for Immunization

The following materials were used for the immunization procedure: Balb C mice, 6 week old females, Freund's adjuvant complete and incomplete (CFA and IFA respectively), Syringes 1 ml, 27 G needles (if not available use 25), and glycated CD59 peptide Materials for Fusion (All Sterile)

The following materials were used for the fusion procedure: Rubber policeman (autoclaved), cell strainer 70 micron from VWR (Bridgeport, N.J.), RPMI media, 50 ml tubes sterile, HAT media: RPMI-1640/10% FBS/Pen/strep/AmphB and HAT (from ATCC, Manassas, Va.), HT media as above but HT instead of HAT (amph B could be omitted if no high risk of fungal contamination).

Method of Immunization

Foot Pad Immunization for Lymph Nodes Extraction (LN)

100 μl of complete adjuvant containing 50 μg peptide antigen was injected into the mouse foot pad and repeated the injection every fourth day. The second injection was done with incomplete adjuvant. After that the injections were done with an equal volume of PBS. The final dose was given at day 17 and the animals were prepared for fusion on day 18.

Method of Fusion

Protocol to Obtain Lymph Nodes

The mice were sacrificed with $CO_2$ and the skin was wet with 70% ETOH. A small incision was made in the right flank and both sides were torn apart. Using a different set of sterile instruments, the lymph node was obtained form the popliteal region. Generally, the lymph node had grown enough and could be visualized directly. Sterile conditions were carefully preserved. The lymph node was then cut or removed with the forceps and was put into a petri dish with RPMI media with no serum. After the lymph node was removed, the serum was obtained from this animal and labeled IMMUNE SERUM as positive control. The lymph nodes were placed in a strainer on top of a 50-ml tube and a rubber policeman was used to gently press the lymph nodes while small amounts of media without serum were added. The cells were counted in the 50-ml tube (those were the lymph nodes and other cells that passed through the strainer). A volume with a number of cells equal to the number of AG8 cells previously counted (in general $2 \times 10^7$ each) was taken.

Preparation of the AG8 Cells (Myeloma Cells)

These cells were grown 1-2 weeks in advance. The day prior to the fusion, fresh media was added to have the cells growing exponentially by the time of the fusion. On the day of the fusion, part of the supernatant was taken out without disturbing the cells that were in suspension (this allowed the reduction of the volume necessary to spin down). The cells were counted in a hemocytometer using tryphan blue to measure viability. More than 80% viable cells were needed to do the fusion. One fusion was done with $2 \times 10^7$ AG8 cells and $2 \times 10^7$ of lymph node or spleen cells obtained from the mouse.

Obtaining Macrophages

The day prior to the fusion, 24-well plates were prepared with macrophage (feeder cells). These macrophage plates were also prepared when doing subcloning or in any circumstances in which it was necessary to pass the clones to a new plate (in the event that macrophages weren't available, the cells were passed without them). Macrophage were obtained from Balb C mouse or the same mouse strain that used to produce the monoclonal antibody. The animal was sacrificed with $CO_2$ and disinfected the skin with 70% ETOH. A small cut was made with sterile instruments in the abdominal skin and both sides were pulled apart exposing the abdominal wall. With a 10 ml syringe and an 18 G needle, 3-5 ml of RPMI media with or without serum was injected into the incision. On the opposite side of the abdominal wall to where the needle is injected, the peritoneal contents were shaken a few times to detach macrophages. Using the same syringe and needle, most of the volume that was previously injected was aspirated, being careful not to damage the intestine to avoid contamination of the sample. The aspirate was added to the 24 ml of media (when only one 24 well plate was prepared) with serum and antibiotics. 1 ml was plated per well and put in the incubator at 37° C. and 5% $CO_2$. This animal was also used to take NON-IMMUNE SERUM.

Fusion of AG8 and Lymph Node Cells.

Approximately $2 \times 10^7$ AG8 were added to the same amount of lymphocytes and mixed together in a 50 or 15 ml tube. Media without serum was added and the mixture centrifuged at <1000 rpm for five minutes. The supernatant was decanted gently and all media was removed. The bottom of the tube was tapped gently with a finger to resuspend the cells. At the same time that the cells were centrifuging, the polyethyleneglycol (PEG) solution was prepared. The PEG solution was heated until it was liquid, then 1 ml of PEG was quickly mixed with 1 ml of RPMI media WITHOUT SERUM. This mix should have had a pinky color. If it was a yellow color, it was too acid and sterile NaOH was added (usually no more than one or two drops or 10-20 µl). When the PEG solution was pink, 1 ml was removed with a 1 ml pipette and added to the cells from the centrifugation step. This step was done gently in no more than 45 seconds. Immediately after adding the PEG, 5 ml of RPMI media WITHOUT SERUM was added to the cell mixture. This was done gently, (slowly over 20 seconds) to avoid osmotic breakdown of the cells. The cell mixture was centrifuged 5 minutes at 1000 rpm and the supernatant decanted. Gently, 4 ml of HAT-media was added, mixed, and then the mixture was transferred to 20 ml of HAT-media making a total of 24 ml. The media was added softly to avoid breaking the hybridomas. Generally, the media was allowed to slide from the side of the tube. 1 ml of this cell suspension was placed in each well of a 24 well plate that already contains 1 ml of macrophage suspension obtained the day before (or the same day), resulting in total of 2 ml of media per well.

Testing Supernatants for Monoclonal Antibodies

After hybridomas were placed in the 24-well plate, the plates were put back at 37° C. Four to five days later, the start of formation of clones could be seen. Approximately at day 6 or 71 ml of media was taken from the top of each well and tested in an ELISA of 96-well plate that had been previously prepared as described. The supernatants that gave a positive result indicated that there was a clone of cells in that well that was producing the desired antibody. Once a positive clone was identified, we proceeded with cloning.

Cloning Hybridomas

The 24-well plate now contained 1 ml of media because 1 ml had been removed to do the ELISA. In the remaining 1 ml in the 24-well plate, the cells were mixed gently with a 1 ml pipette. 500 µl was removed and placed in 24 ml of HT-media. One ml of that cell suspension was placed in each well of 24-well plate, which was labeled as the EXPANSION colony. The remaining 500 µl left in the 24-well plate were used for cloning in 96-well plates as follows.

Cloning Procedure

Two different methods were used. The 1000, 100, 50 cells-per-plate method and the 500 and 50 cells-per-plate method.

The number of cells left in the 500 µl were counted and a cell suspension that had $1-5 \times 10^4$ cells/ml was prepared. 10.8 ml of HT media was added to 1.2 ml of the $1-5 \times 10^4$ cells/ml ($1-5 \times 10^3$ cells/ml). A different dilution was also done by using 1000 cells in 11 ml of HT media). 100 µl/well was plated in the 96-well plate with macrophages. 9.6 ml of media was added to the remaining 2.4 ml (1/5 dil) for a final cell concentration of $2-10 \times 10^2$ cells/ml and 100 µl was added to a new 96-well plate. One ml of the media left from the cell suspension step (above) was taken and added to 10 ml of HT media. 100 µl of this mixture was added per well.

To remaining 2.4 ml 9.6 ml of medium was added (for a final amount of cells between 40 and 200 cells per plate) and 100 µl of cells was added to each well. The cells were placed back in the incubator and checked 5-6 days later for colonies. The supernatant from the 24-well plate (expansion) and from the 96 wells with colonies on it was tested.

Positive Clone is Identified: Expansion Protocol

After a positive hit was identified from the cloned cells in the 96-well plate with 40-200 cells per plate, that positive clone was expanded. If there was a clone from the 24-well plate used for expansion, those cells needed to be cloned again. If there was a hit in the 96-well plate and this was a clone, then the clone was expanded using the following protocol. The cells were allowed to grow until there were enough in the well to pass. The cells were transferred to a 6-well plate with macrophages on it. This was done by: taking the 100 µl of cell suspension from the well into 12 ml of HT media, adding 2 ml of cell suspension to each well, allowing the cells to grow. After 5 days the supernatant was checked in an ELISA. When there were a large number of cells in each well ($5 \times 10^6$) cells that tested positive in half of the wells were taken and frozen in 10% DMSO-HT media. Cells were taken from another well of the plate and plated in another 6 well plate. Then cells from another well were injected into the peritoneum of Balb C mouse to produce ascites. Cells could also be grown in special flasks and media.

Antibody Purification

After obtaining supernatants or ascitic fluid ammonium sulfate precipitation was performed. Ammonium sulfate was slowly added to the samples until approx. 30-40% vol/vol. The sample was centrifuged at 5000 rpm for 5 minutes, and the precipitate was saved. The supernatant was reused and an additional 10-20% ammonium sulfate was added to the supernatant. The pellet was resuspended in PBS and dialyzed extensively against PBS. Final purification utilized a Protein A column and an immunoaffinity column with non-glycated peptide as solid phase. The purified monoclonal antibody selected is an IgGi derived from clone 7 (C7). The hybridoma that produces the antibody Clone 7 was deposited with the American Type Culture Collection (ATCC; P.O. Box No. 1549, Manassas, Va. 20108, USA) in Manassas, Va. on Jun. 1, 2004, and has been assigned ATCC Patent Depository Number: PTA-6023.

Specificity of the Anti-glycCD59 mAb Selected

The specificity of the C7 monoclonal antibody to recognize glycated CD59 in human urine was determined by Western Blot Analysis using a combination of three antibodies:
1) Mouse anti-human CD59 mAb (this is a commercially available monoclonal antibody specific for human CD59 (BRIC 229: mouse IgG2b anti-CD59 antibody; IBGRL Research Products, UK)
2) Rabbit anti-glucocytol lysine Ab (an antibody specific for glycated lysine residues in any protein)
3) Mouse anti-glycated CD59 mAb (C7, clone 7).

Urine samples from diabetic and non-diabetic subjects were concentrated 5-fold by centrifugation through a 5,000 molecular weight cut-off filter, and concentrates subjected to SDS-gel electrophoresis run in parallel in two gels. Then the gels were transferred into nitrocellulose membranes and immunoblotted:
1) One membrane was blotted with Bric 229 anti-CD59 antibody plus a goat anti-mouse antibody labeled with green fluorescence.
2) The other membrane was blotted twice: first with the mouse anti-glycated CD59 (clone 7) mAb plus a secondary goat anti-mouse antibody labeled with green fluorescence; and secondly with rabbit anti-glucocytol lysine Ab plus a secondary donkey anti-rabbit antibody labeled with red fluorescence. Membranes were then scanned using an Odyssey Double Channel Laser Scanner (LICOR Bioscience, Lincoln, Nebr.), which allows the independent scanning of the green and red fluorescence.

The results indicated that all urines contained comparable amounts of CD59 ($\approx$19 Kd band in the anti-CD59 blot). The anti-glycated CD59 mAb (C7) labeled a 19 kd band that was present only in the diabetic urine sample. This band was also present in the diabetic but not the non diabetic urines blotted against the anti-glucocytol-lysine mAb. The results indicated that the antibodies were recognizing the same protein in the gels. In summary, in all urine samples processed there was CD59, which was glycated only in the diabetic subject. Glycated CD59 but not non-glycated CD59 was recognized by the C7 anti-glycated CD59 mAb.

Immunocytochemistry Detection of Glycated CD59 in Diabetic Kidneys

The specificity of the antibody to recognize glycated CD59 in diabetic tissues was established in kidney biopsy samples from diabetic and non-diabetic subjects. Serial sections of para-aldehyde fixed paraffin embedded kidney biopsy samples were immuno-stained with a) secondary antibody only as negative control, b) with Bric 229 anti-CD59 antibody, and c) with anti-glycated CD59 antibody (C7, clone 7). The results indicated that there was CD59 present in both non-diabetic and diabetic samples; in contrast, glycated-CD59 was only present in the diabetic sample.

Example 2

Experiments were performed to investigate the detection of glycated CD59, the complement regulatory protein that inhibits formation of the MAC. The glycated form of CD59 is inhibited by glycation.

Methods

An antibody was generated that would recognize the glycated form of human CD59 but not the non-glycated form nor other glycated proteins. To raise this antibody a peptide was synthesized that encompassed the glycation site formed by amino acid residues lysine 41 and histidine 44. The peptide contained a glycated lysine ($K_{glu}$) in position 41 and two cysteine residues were replaced by alanine residues to avoid formation of disulfide bridges. The peptide (termed $CD59_{36-49}$-$K41_{(glu)}$) was synthesized by solid phase methodology, purified by affinity chromatography and the structure of the purified synthetic peptide confirmed by mass spectrometry.

Two rabbits were immunized with the human $CD59_{36-49}$-$K41_{(glu)}$ peptide and the antibody titer detected by ELISA using the same peptide as standard. Non-immune serum obtained before immunization was kept for negative controls. The rabbit serum demonstrating high levels of anti-$CD59_{36-49}$-$K41_{(glu)}$ was collected and the anti-$CD59_{36-49}$-$K41_{(glu)}$-specific immunoglobulin IgG fraction was purified by affinity chromatography using $CD59_{36-49}$-$K41_{(glu)}$ attached to a solid phase support.

Figure 3:
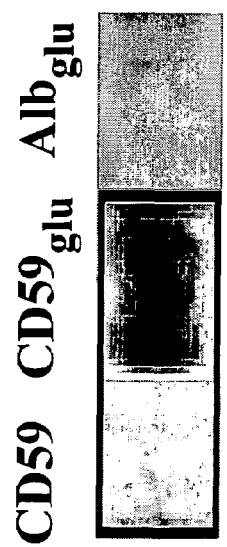
FIG. 3 is a digitized image of a Western blot and a table indicating results of an ELISA using the anti-glycated CD59 antibody.

The specificity of the anti-glycated human CD59 antibody was documented. Human CD59 purified from human red blood cells and then glycated in vitro by exposure to glucose 0.5M for variable times. The specificity of the antibody was then documented by both Western blot analysis and ELISA (FIG. 3). FIG. 3A shows that the anti-glycated CD59 antibody recognizes purified human CD59 after but not before glycation and does not recognize another glycated protein such as glycated albumin [purchased from Sigma Co (St. Louis, Mo.) and routinely used as a standard for glycated proteins]. Glycation in CD59 occurred in lysine 41 because the anti-glycated CD59 antibody did not recognized the human CD59 mutant (in which lysine 41 was replaced by alanine) after exposure to glucose for a similar time interval.

The anti-glycated CD59 antibody was used to measure by ELISA the presence of glycated CD59 in human urine. An ELISA using an antibody against total CD59 was also applied to the samples and the results expressed as the ratio of glycated-CD59/Total CD59 (i.e. the relative amount of glycated CD59 in each urine sample). Urine samples were from non-diabetic and diabetic subjects. The results indicated that glycated CD59 was found in human urine and that it correlated well with the levels of glycated hemoglobin (HbA1C) in blood, the current clinical standard for assessment of glycemic exposure in diabetic patients.

The anti-glycated CD59 antibody was used to measure by ELISA the presence of glycated CD59 in human plasma. An ELISA using an antibody against total CD59 was also applied to the samples and the results expressed as the ratio of glycated-CD59/Total CD59 (i.e. the relative amount of glycated CD59 in each plasma sample). Plasma samples from non-diabetic and diabetic subjects were obtained by centrifugation (for 5 minutes at 100 g) of a sample of blood treated with EDTA to avoid clotting. The results indicated that glycated CD59 was found in human plasma and that it correlated well with the levels of glycated hemoglobin (HbA1C) in blood, the current clinical standard for assessment of glycemic exposure in diabetic patients.

The antiglycated CD59 antibody was used to detect the presence of glycated CD59 in diabetic kidneys. The samples were paraffin blocks from diabetic patients that underwent a renal biopsy because of renal failure and to detect diabetic nephropathy (also known as glomerulosclerosis). The samples were obtained from a collection of renal biopsies kept in the Pathology Department of Brigham and Women's Hospital, Boston, Mass. The paraffin blocks were sectioned, paraffin removed by standard methods and then the thin sections stained with anti-glycated CD59 antibody, with anti-MAC antibody and with the IgG fraction of the rabbit serum extracted before immunization (non-immune serum used as a negative control). The results indicated that glycated CD59 is present in diabetic kidneys and colocalizes with MAC. In this experiment, 8 out of 13 diabetic subjects (70%) showed glycated CD59 in renal glomeruli whereas none of 7 subjects with other forms of renal disease (sufficient to require a renal biopsy) showed any staining. Diabetic nephropathy is one of the most serious diabetic complications, the number one cause of renal failure and renal transplants in the adult population of the United States.

The antiglycated CD59 antibody was used to detect the presence of glycated CD59 in diabetic nerves. The samples were paraffin blocks from diabetic patients that underwent a sural nerve biopsy because of diabetic neuropathy. The samples were obtained from a study of diabetic nerves conducted by Dr. Arthur Hays, Chief of Neuropathology at the Columbia Presbyterian Hospital in New York, N.Y. The paraffin blocks were sectioned, paraffin removed by standard methods and then the thin sections stained with anti-glycated CD59 antibody, with anti-MAC antibody, with an anti-ULEX antibody that specifically recognizes the human endothelium (this was to label and identify the blood vessels within the nerve) and with the IgG fraction of the rabbit serum extracted before immunization (non-immune serum used as a negative control). The results indicated that the micro-vessels identified by staining with anti-ULEX antibodies also stain positive for glycated CD59 which colocalizes with MAC. In this experiment, 8 out of 12 diabetic subjects (70%) showed glycated CD59 in sural nerves whereas none of 14 subjects with other forms of neuropathy (sufficient to require a nerve biopsy) showed any staining. Diabetic neuropathy is another of the most serious diabetic complications.

The antiglycated CD59 antibody was used to detect the presence of glycated CD59 in diabetic micro-vessels from a diabetic foot. The samples were paraffin blocks from diabetic patients that underwent a tissue biopsy because of diabetic peripheral artery disease. The samples were obtained from a study of diabetic blood vessels conducted by Dr. Michael Conti, at Brigham and Women's Hospital, Boston, Mass. The paraffin blocks were sectioned, paraffin removed by standard methods and then the thin sections stained with anti-glycated CD59 antibody, with anti-MAC antibody, with an anti-ULEX antibody that specifically recognizes the human endothelium (this is to label and identify the blood vessels within the nerve) and with the IgG fraction of the rabbit serum extracted before immunization (non-immune serum used as a negative control). The results indicated that the micro-vessels identified by staining with anti-ULEX antibodies also stain positive for glycated CD59 which colocalizes with MAC. In this experiment, 5 out of 5 diabetic subjects (100%) showed glycated CD59 in micro-vessels whereas none of 4 subjects with other forms of arterial disease (sufficient to require a biopsy) showed any staining. Diabetic micro-vascular is another of the most serious diabetic complications.

The results indicated that glycated CD59 has been identified in the main target organs of the diabetic complications as well as in urine and plasma of diabetic patients.

In view of the presence of glycated CD59 in human diabetic urine and/or plasma, the strong correlation with glycated hemoglobin (HbA1c), the current clinical standard for clinical assessment of glycemic load in diabetics, the results and data presented above demonstrated the human diagnostic value and efficacy in assessing glycemic control.

Glycated CD59 is a likely mediator of the vascular complications of diabetes. In contrast, glycated hemoglobin is only a by-stander with no recognized action in the pathogenesis of the disease. In view of the pathogenic role that glycated CD59 and the complement system may play in the development of vascular diabetic complications and the absence of any pathogenic role of HbA1c, the measurement of glycated CD59 in urine and/or plasma a provides a better clinical test indicative of glycemic control and of the susceptibility of a diabetic subject to develop diabetic vascular complications.

Example 3

Experiments were performed to detect levels of glycated and nonglycated CD59 in saliva samples. Results indicated that the methods of assessing levels of glycated and nonglycated CD59 could be used for tissues and fluids other than urine and blood, such as saliva, in addition to being used for tissues, urine, and blood samples.

Methods

Each experiment described below herein involved the detection of glycated CD59, the complement regulatory protein that inhibits formation of the MAC. The initial step in the experiments included the generation of an antibody that recognizes the glycated form of human CD59 but does not recognize the non-glycated form or other glycated proteins. To raise this antibody a peptide was synthesized encompassing the glycation site formed by amino acid residues lysine 41 and histidine 44 and containing a glycated lysine ($K_{glu}$) in position 41. In addition, two cysteine residues in the peptide were replaced by alanine residues to avoid formation of disulfide bridges. The peptide (termed $CD59_{36\text{-}49}\text{-}K41_{(glu)}$) was synthesized by solid phase methodology, purified by affinity chromatography, and the structure of the purified synthetic peptide confirmed by mass spectrometry.

An anti-glycated human CD59 antibody was prepared. For this process, two rabbits were immunized with the human $CD59_{36\text{-}49}\text{-}K41_{(glu)}$ peptide and the antibody titer detected by ELISA using the same peptide as standard. Non-immune serum obtained before immunization was kept for negative controls. The rabbit serum demonstrating high levels of anti-$CD59_{36\text{-}49}\text{-}K41_{(glu)}$ was collected and the anti-$CD59_{36\text{-}49}\text{-}K41_{(glu)}$ specific immunoglobulin IgG fraction was purified by affinity chromatography using $CD59_{36\text{-}49}\text{-}K41_{(glu)}$ attached to a solid phase support.

The specificity of the anti-glycated human CD59 antibody was documented. .Human CD59 was purified from human red blood cells and then glycated in vitro by exposure to 0.5M glucose for variable times. The specificity of the antibody was then documented by both Western blot analysis (FIG. 3A) and ELISA (FIG. 3B). FIG. 3 shows that the anti-glycated CD59 antibody recognizes purified human CD59 after but not before glycation and does not recognize another glycated protein such as glycated albumin (purchased from Sigma-Aldrich, St. Louis, Mo., and routinely used as a standard for glycated proteins). Glycation in CD59 occurs in lysine 41 because the anti-glycated CD59 antibody did not recognized the human CD59 mutant (in which lysine 41 was replaced by alanine) after exposure to glucose for a similar time interval.

The anti-glycated CD59 antibody was used to detect by immunoblotting the presence of glycated CD59 in human saliva. Saliva samples were from non-diabetic subjects and from diabetic subjects. Purified recombinant human CD59 (non glycated) was included as a positive control. The results indicated that glycated CD59 was found in human saliva of diabetic but not of non-diabetic subjects.

Glycated CD59 may mediate the vascular complications of diabetes. In contrast, glycated hemoglobin (HbA1c) has no recognized action in the pathogenesis of the disease. In view of the pathogenic role that glycated CD59 and the complement system may play in the development of vascular diabetic complications and the absence of any pathogenic role of HbA1c, the measurement of glycated CD59 in urine and/or plasma and/or tissue and/or saliva was determined to be useful clinical indicator of glycemic load and of the susceptibility of a diabetic subject to develop diabetic vascular complications.

Example 4

Introduction

To investigate whether in vitro glycation of human CD59 inhibits its homologous restriction activity a functional assay of glycated CD59 was performed. A 10% cell suspension of guinea pig erythrocytes (GPE) was incubated with purified CD59 previously exposed for different time intervals to the glycating sugars glucose (0.5M) or ribose (0.5M), or to non-glycating sorbitol (0.5M) to control for the high osmolarity of the medium. The sensitivity of the GPE to human membrane attack complex (MAC) was tested using purified human C5b6 and C7, C8 and C9 (Halperin et al, 1993a). The number of CD59 molecules incorporated per GPE was determined with 125I-CD59 before and after glycation with ribose.

Methods

CD59 purification: CD59 from urine was isolated by anion exchange chromatography using a DEAE protein-Pak HR 8 column (Waters Corp., Milford, Mass.) as described in Davies et al, 1998. CD59 from butanol extracts of RBC and lysates of CHO cells was purified by immunoaffinity chromatography (see: Davies et al, 1998, Hughes et al, 1992, and van den Berg et al, 1993) using the monoclonal rat anti-human CD59 antibody YTH 53.1 (Serotec Inc. Raleigh, N.C.), as in Fletcher, et al., 1994. Protein concentration was estimated by the micro-BCA protein assay (Pierce Chemical Co. Rockford, Ill.). Western blots were performed on proteins separated by SDS-PAGE using the Supersignal detection system (Pierce Chemical Co.).

Functional Activity Assays: Hemolysis Protection Assay

Activity of purified CD59 and its mutants before and after glycation was determined by a hemolysis protection assay using guinea pig erythrocytes (GPE) exposed to the terminal complement proteins C5b6, C7, C8 and C9 to form the MAC, as described in Benzaquen, et al, 1994 and Halperin et al., 1993b. In this assay, ~10-3 unit of human C5b6 was required to lyse 50% of a GPE cell suspension (one unit is the amount of C5b6 required to lyse 50% of a human RBC suspension [Haperin et al, 1993a]). The activity of purified CD59 was defined as the difference between the percent lysis of the unprotected GPE minus the percent lysis of the CD59-protected GPE.

In Vitro Glycation

Purified CD59 (10-30 µg/ml) was incubated for different time intervals at 37° C. in 0.5 M of either reducing monosaccharides (glucose, ribose, or glucose-6-phosphate) or the non-glycating sorbitol to control for potential osmotic effects.

Incorporation of CD59 into GPE

Purified CD59 was iodinated with 125I (NEN® Life Science Products Inc. Boston, Mass.) using Iodobeads (Pierce Chemical Co.). Iodination of CD59 did not affect either its homologous restriction activity or its sensitivity to glycation-inactivation. After incubation of GPE with 125I-CD59, the cells were washed extensively to remove unbound CD59, lysed and the radioactivity incorporated was measured in a gamma counter. Using standard methods, the number of CD59 molecules incorporated per GPE was calculated from the specific activity of the 125I-CD59 preparation (150 cpm/ng) and the hematocrit of the GPE suspension.

Results

Figure 4:
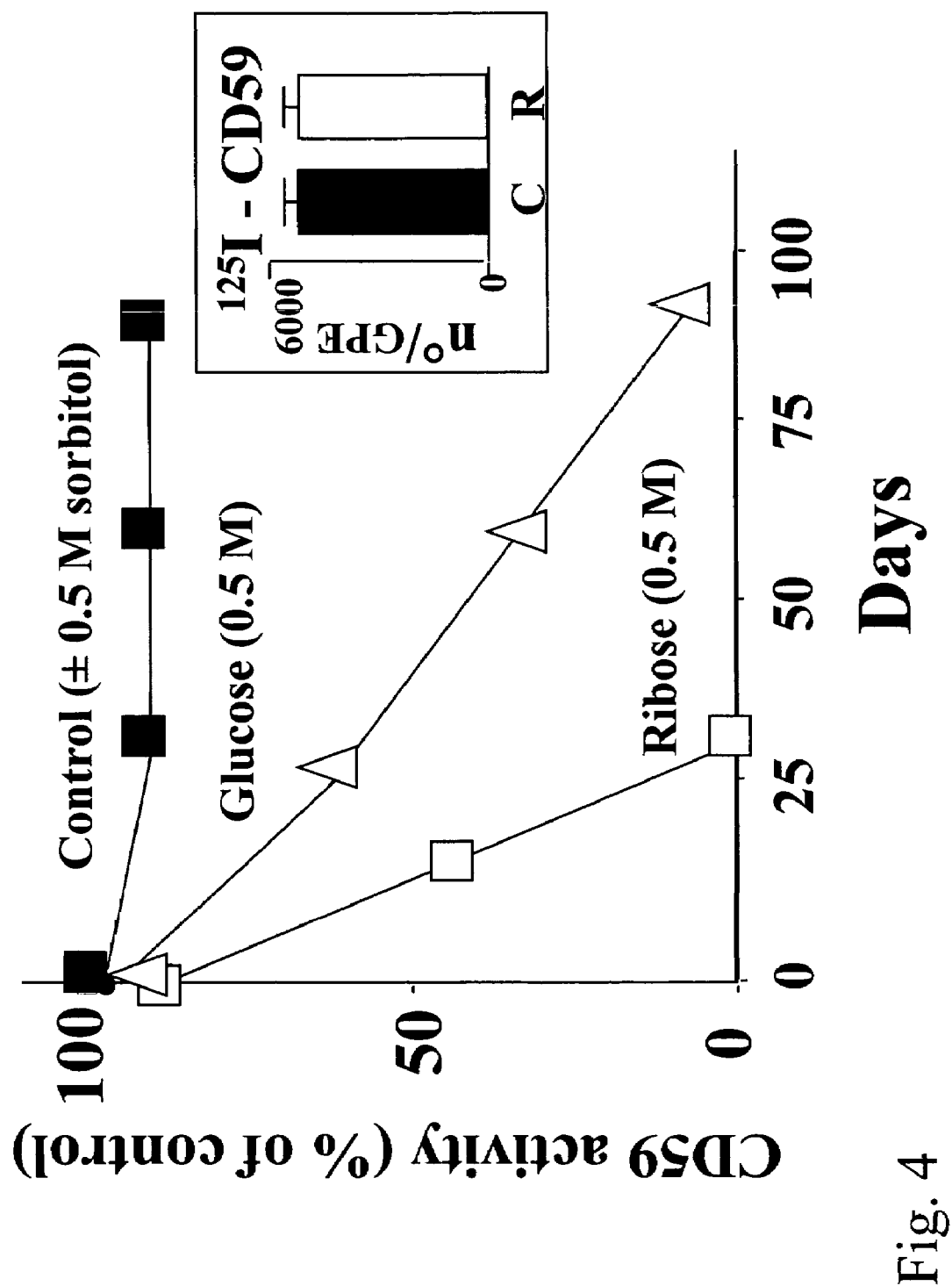
FIG. 4 is a graph indicating CD59 activity as a percent of control activity for a cell suspension of GPE incubated with purified CD59 previously exposed for different time intervals to the glycating sugars glucose (open triangles, 0.5M) or ribose (open squares; 0.5M), or to non-glycating sorbitol (closed squares, 0.5M). Data points represent the mean of triplicate determinations (SEM are smaller than data points).

Glycation abrogates the homologous restriction activity of human CD59. The results, illustrated in FIG. 4, demonstrate that incubation of CD59 with the glycating sugars glucose and ribose significantly reduce the CD59 activity.

Example 5

Introduction

To determine the location of the site that when glycated inactivates the CD59 molecule, replacement by site-directed mutagenesis of either K41 or H44 was performed. Wild type (WT) and CD59 mutants Gln-41 and Gln-44 were expressed in CHO cells and purified by affinity chromatography. The activity of the mutant CD59 molecules was tested in the GPE hemolytic assay before and after glycation with ribose for different time intervals.

Methods

Expression and Purification Assays

Using standard methods, wild-type and mutant CD59 cDNAs were subcloned into the mammalian expression vector pSVK3 (Amersham Pharmacia Biotech Inc. Piscataway, N.J.) and transfected into CHO cells together with the selection marker pBABE, which confers resistance to puromycin. Expression and functionality of the WT and mutant CD59 in the puromycin resistant clones were tested by Western blot analysis, immunohistochemistry in non-permeabilized cells using the YTH 53.1 antibody and a Texas Red conjugated secondary antibody, and a functional dye release assay, which measures protection against human complement, as described in Zhao et al., 1991.

Site-directed Mutagenesis

Plasmid pK562-3 containing the cDNA of human CD59 (Philbrick, et al., 1990) was obtained from ATCC. Site-directed mutagenesis to substitute residue K41 or H44 for glutamine (Gln) was performed using the Altered Sites 11 system (Promega Corp. Madison, Wis.). The mutagenic primers used were 5'-GTC GTT GAA ATT ACA ATG CTC AAA CTG CCA ACA CTT-3' (SEQ ID NO: 11) for the Gln-41 substitution, and 5'-GTT GAA ATT GCA CTG CTC AAA CTT CCA-3' (SEQ ID NO: 12) for the Gln-44 mutation. Successful mutagenesis was confirmed by sequencing using standard methods.

For description of CD59 purification, in vitro glycation, and hemolysis protection assay: See Example 4, Methods.

Results

Replacement by site-directed mutagenesis of either K41 or H44 abolished the sensitivity of human CD59 to glycation-inactivation confirming that the K41-H44 motif constitute a glycation-inactivation site. Results of the GPE lysis assay and the CD59 activity assay are illustrated in FIG. 5.

Example 6

Introduction

To determine whether glycation of human endothelial cells and human red blood cells (RBC) results in the inactivation of CD59, an experiment was designed to detect whether glycation would render human endothelial cells and human red blood cells (RBC) more sensitive to MAC-mediated growth factor release or MAC-mediated lysis. Both the endothelial cells and the RBC were glycated and exposed to purified terminal complement components C5b6, C7, C8, and C9 to form the MAC and the mitogenic activity in the conditioned medium was measured.

Methods

Glycation of RBC

A 10% RBC suspension was incubated with or without ribose (50 mM) for 48 hours at room temperature, followed by 20 min incubation with cyanoborohydride (20 mM). Cell volume was then adjusted by the nystatin procedure (described in Halperin, et al, 1987) and the osmotic fragility of the cell suspension was measured by standard procedures. To ascertain that differential sensitivity to lysis was not caused by an increased osmotic fragility of RBC exposed to glycating agents, RBC were only used when average cell volume and osmotic fragility were similar to that of control cells.

Glycation of HUVEC

Confluent second passage HUVEC were incubated with or without ribose (50 mM) for 24 hr (370°, 5% $CO_2$) followed by 20 min incubation with cyanoborohydride (20 mM). Cells were then exposed to purified terminal complement proteins to form the MAC, aliquots of conditioned media separated to test for mitogenic activity in indicator quiescent 3T3 cells, as described in Benzaquen et al, 1994.

RBC and HUVEC Analysis

To avoid confounding effects of colloidosmotic swelling caused by the glycating agent, cell volume was adjusted in all cells, glycated and non-glycated prior to assaying for sensitivity to MAC-induced lysis (Halperin, et al, 1987). After volume adjustment, aliquots of glycated and non-glycated cells were separated for rescue with purified CD59 (4 µg), exposure to neutralizing anti-CD59 antibody (YTH53.1) or both, and then exposed to purified C5b6, C7, C8 and C9 to form the MAC.

Results

The data indicate that glycation of the endothelial calls and RBC makes them more sensitive to MAC-mediated growth factor release and MAC-mediated lysis (see FIG. 6). Results are expressed as the ratio of mitogenic activity released into the conditioned media in the presence or absence of MAC.

Example 7

Introduction

To determine whether glycated CD59 is present in human urine, which indicates that glycation occurs in vivo, urine from a nondiabetic subject was concentrated, fractionated, and tested for the presence of CD59 using an anti-CD59 specific antibody. The CD59 positive fractions were then purified further and probed with an antibody that specifically recognizes the reduced ketoamine of glycated lysine residues and binds to the glycated region of CD59, to determine whether glycated CD59 was present in the sample.

Methods

For details of the CD59 purification, see Example 4, Methods section. Inmunoblotting with anti-hexitol-lysine antibody was performed using standard procedures as described in Myint, et al, 1995.

Results

The CD59 isolated from a non-diabetic subject was immunoblotted with the anti-hexitol-lysine antibody, which recognizes the glycatedCD59. The results illustrated in FIG. 7 demonstrate that glycated CD59 is present in human urine.

Example 8

Introduction

Following the identification of glycated CD59 in human urine, the levels present in urine were measured to determine whether levels of glycated CD59 correlate with levels of glycated hemoglobin (HbA I c) in diabetic and nondiabetic subjects. Concentrated human urine from either normoglycemic or hyperglycemic (diabetic) individuals was separated by. anion exchange chromatography, and a CD59-positive fractions were immunoprecipitated with a monoclonal anti-CD59 antibody. The antibody was used because it binds to an epitope distant from the K41-H44 putative glycation motif on CD59 and was, therefore expected to precipitate both glycated and non-glycated CD59. An aliquot of the immunoprecipitate was separated by SDS-PAGE and blotted with the monoclonal anti-CD59 antibody YTH53.1.

Methods

For detail of CD59 purification and quantification see Example 4, Methods section. Measurements of HbA1c were performed using standard procedures at the Joslin Diabetic Center (Boston, Mass.). For details of immunoblotting with anti-hexitol-lysine antibody, see Example 7, Methods section.

Results

Comparison of the levels of glycated CD59 and glycated hemoglobin from diabetic and nondiabetic subjects indicate that the levels of glycated CD59 correlate with the levels of glycated hemoglobin (see FIG. 7).

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference in their entirety.

I claim:

1. An isolated antibody produced by the hybridoma deposited as ATCC Patent Depository Number PTA-6023, or an antigen-binding fragment thereof.

2. The isolated antibody or antigen-binding fragment thereof of claim 1, attached to a detectable label.

3. The isolated antibody or antigen-binding fragment thereof of claim 2, wherein the detectable label is selected from the group consisting of a fluorescent label, an enzyme label, a radioactive label, a nuclear magnetic resonance active label, a luminescent label, and a chromophore label.

4. The isolated antibody or antigen-binding fragment thereof of claim 1, wherein the antibody or antigen-binding fragment thereof is lyophilized.

5. The isolated antibody or antigen-binding fragment thereof of claim 1, wherein the antibody or antigen-binding fragment thereof is in an aqueous medium.

6. The isolated antibody or antigen-binding fragment thereof according to claim 1, wherein the antibody or antigen-binding fragment thereof binds to a conformational epitope.

7. A kit for detecting the presence of glycated CD59 comprising a package including a container containing the isolated antibody or antigen-binding fragment thereof of claim 1, and instructions for use of the antibody or antigen-binding fragment thereof to detect the presence of glycated CD59.

8. The kit of claim 7, wherein the antibody or antigen-binding fragment thereof is attached to a detectable label.

9. The kit of claim 8, wherein the detectable label is selected from the group consisting of a fluorescent label, an enzyme label, a radioactive label, a nuclear magnetic resonance active label, a luminescent label, and a chromophore label.

10. The kit of claim 7, wherein the antibody or antigen-binding fragment thereof is lyophilized.

11. The kit of claim 7, wherein the antibody or antigen-binding fragment thereof is packaged in an aqueous medium.

12. The kit of claim 7, further comprising a container containing a second antibody or antigen-binding fragment thereof that specifically binds non-glycated CD59 or non-K41-glycated CD59, and instructions for using the second antibody as a control antibody.

13. A kit comprising a package including a container containing a hybridoma that comprises a nucleic acid sequence that encodes the antibody of claim 1, and instructions for producing the antibody.

14. A hybridoma that is deposited as ATCC Patent Depository Number PTA-6023.

15. An isolated antibody or an antigen-binding fragment thereof which specifically binds glycated CD59, wherein the antibody or the antigen-binding fragment thereof competitively inhibits the binding of an antibody produced by the hybridoma deposited as ATCC Patent Depository Number PTA-6023 to glycated CD59.

* * * * *